(12) United States Patent
Mizusawa

(10) Patent No.: US 9,810,886 B2
(45) Date of Patent: *Nov. 7, 2017

(54) WIDE ANGLE OPTICAL SYSTEM

(71) Applicant: OLYMPUS CORPORATION, Hachioji-shi, Tokyo (JP)

(72) Inventor: Masayuki Mizusawa, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/582,633

(22) Filed: Apr. 29, 2017

(65) Prior Publication Data

US 2017/0235132 A1    Aug. 17, 2017

Related U.S. Application Data

(63) Continuation of application No. PCT/JP2016/067388, filed on Jun. 10, 2016.

(30) Foreign Application Priority Data

Jun. 16, 2015 (JP) ................. 2015-121166

(51) Int. Cl.
*G02B 13/04* (2006.01)
*G02B 13/06* (2006.01)
(Continued)

(52) U.S. Cl.
CPC ............. *G02B 13/04* (2013.01); *G02B 9/64* (2013.01); *G02B 13/0055* (2013.01);
(Continued)

(58) Field of Classification Search
CPC .. G02B 13/0055; G02B 13/007; G02B 13/04; G02B 13/06; G02B 17/086;
(Continued)

(56) References Cited

U.S. PATENT DOCUMENTS 5,473,474 A    12/1995    Powell
5,745,302 A     4/1998    Ohno
(Continued)

FOREIGN PATENT DOCUMENTS

EP    2163933 A1    3/2010
EP    2385406 A1    11/2011
(Continued)

OTHER PUBLICATIONS

International Search Report (ISR) and Written Opinion dated Aug. 2, 2016 issued in International Application No. PCT/JP2016/067388.

*Primary Examiner* — Jordan Schwartz
(74) *Attorney, Agent, or Firm* — Holtz, Holtz & Volek PC

(57) ABSTRACT

The wide angle optical system includes in order from a side of an object in front, a first lens group having a negative refractive power, a second lens group having a catadioptric optical element, an aperture stop, and a third lens group having a positive refractive power, and the catadioptric optical element has a first surface, a second surface, and a third surface, and the first surface has a first transmitting surface and a first reflecting surface, the second surface has a second transmitting surface and a second reflecting surface, and the third surface has a third transmitting surface, and the third transmitting surface is a side surface of a circular truncated cone, and the following conditional expressions (1), (2), and (3) are satisfied:

$$\upsilon p < \upsilon n \quad (1),$$

$$|\phi p| < |\phi n| \quad (2), \text{ and}$$

$$90° - \theta k < \alpha/2 \quad (3).$$

7 Claims, 16 Drawing Sheets

(51) Int. Cl.
  *G02B 9/64* (2006.01)
  *G02B 17/08* (2006.01)
  *G02B 27/00* (2006.01)
  *G02B 13/00* (2006.01)

(52) U.S. Cl.
  CPC ........... *G02B 13/06* (2013.01); *G02B 17/086* (2013.01); *G02B 27/0081* (2013.01)

(58) Field of Classification Search
  CPC .. G02B 17/0856; G02B 27/0081; G02B 9/60; G02B 9/62; G02B 9/64; G02B 13/0045; G02B 13/0065; G02B 13/009; G02B 15/14
  See application file for complete search history.

(56) References Cited

U.S. PATENT DOCUMENTS

| | | | |
|---|---|---|---|
| 6,333,826 B1 | 12/2001 | Charles | |
| 6,341,044 B1 | 1/2002 | Driscoll et al. | |
| 6,449,103 B1 | 9/2002 | Charles | |
| 6,611,282 B1 | 8/2003 | Trubko et al. | |
| 8,462,195 B2 | 6/2013 | Yeh et al. | |
| 9,563,040 B2* | 2/2017 | Mizusawa | A61B 1/00 |
| 2002/0012059 A1 | 1/2002 | Wallerstein et al. | |
| 2004/0254424 A1 | 12/2004 | Simkulet et al. | |
| 2006/0238879 A1 | 10/2006 | Togino | |
| 2008/0247062 A1 | 10/2008 | Mizusawa | |
| 2009/0082629 A1* | 3/2009 | Dotan | A61B 1/00096 600/160 |
| 2010/0007969 A1 | 1/2010 | Togino | |
| 2010/0091385 A1 | 4/2010 | Togino | |
| 2010/0195007 A1* | 8/2010 | Takahashi | A61B 1/00096 349/16 |
| 2011/0075273 A1 | 3/2011 | Mizusawa | |
| 2011/0279915 A1 | 11/2011 | Mizusawa | |
| 2015/0265136 A1 | 9/2015 | Honda | |
| 2016/0377842 A1* | 12/2016 | Choi | G02B 13/0065 348/340 |

FOREIGN PATENT DOCUMENTS

| | | |
|---|---|---|
| EP | 2929830 A1 | 10/2015 |
| JP | 2008257121 A | 10/2008 |
| JP | 2008309861 A | 12/2008 |
| JP | 2010224010 A | 10/2010 |
| JP | 2011048086 A | 3/2011 |
| JP | 2011075915 A | 4/2011 |
| JP | 2013255820 A | 12/2013 |
| WO | 2008153114 A1 | 12/2008 |
| WO | 2010084914 A1 | 7/2010 |
| WO | 2014088076 A1 | 6/2014 |

\* cited by examiner

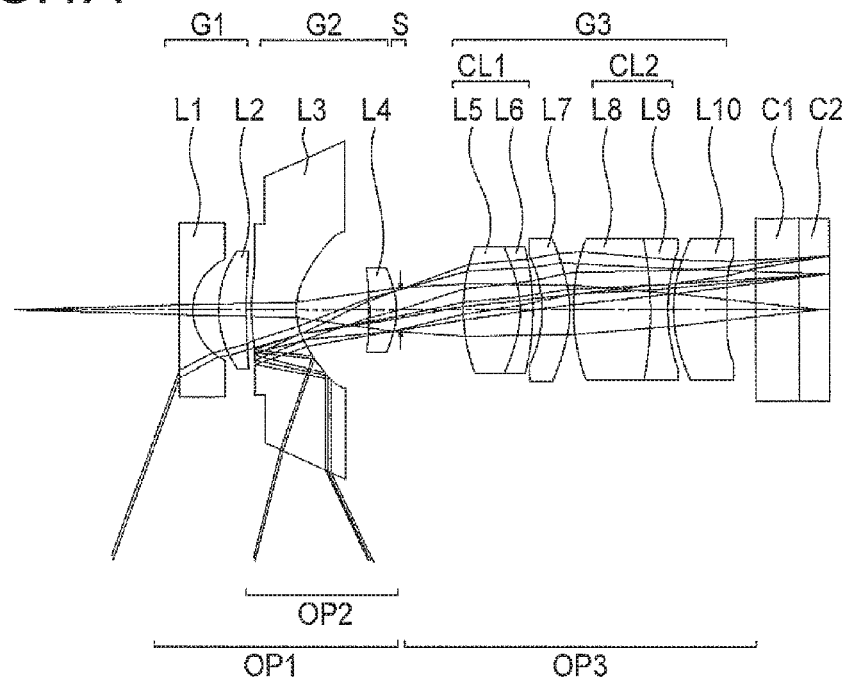
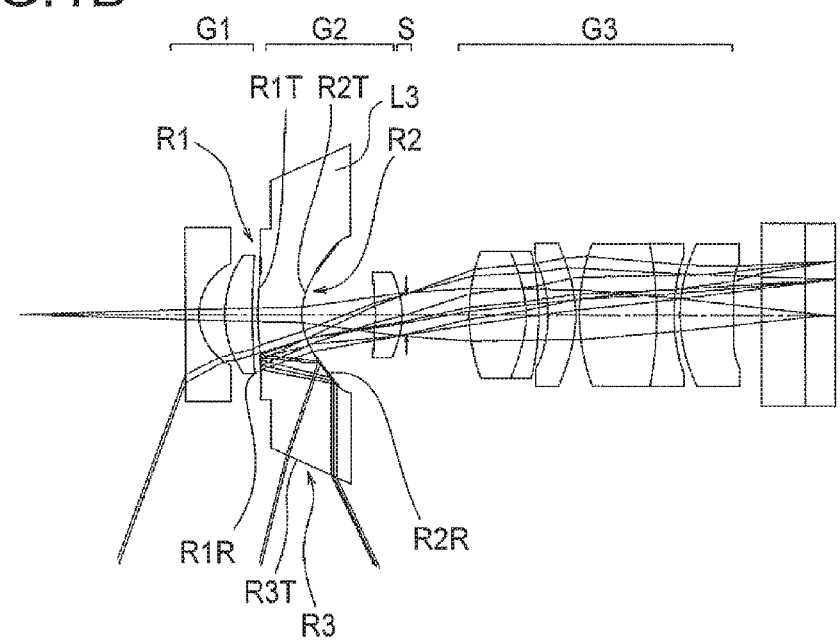

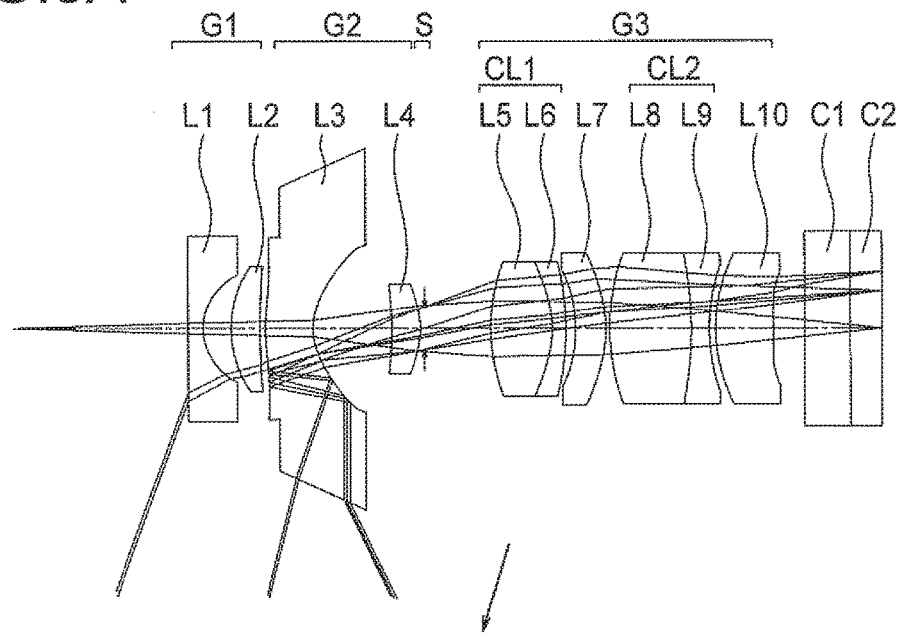
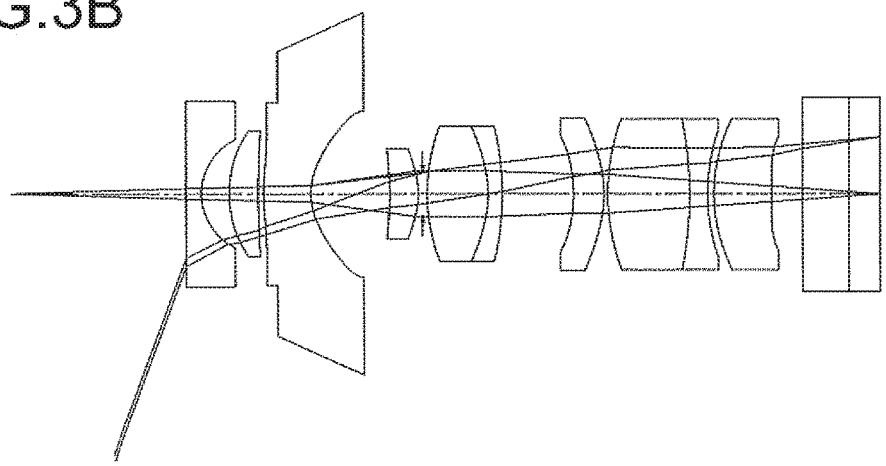

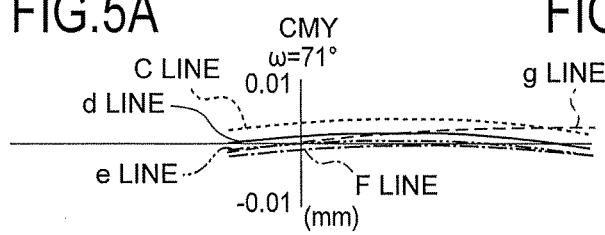
FIG.5A CMY ω=71°
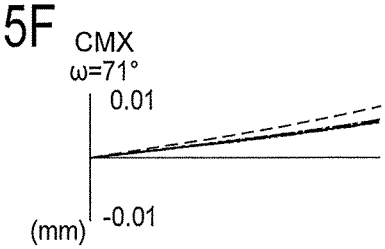
FIG.5F CMX ω=71°
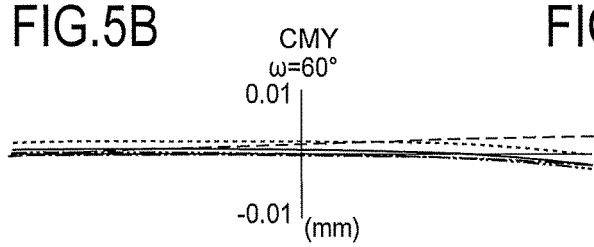
FIG.5B CMY ω=60°
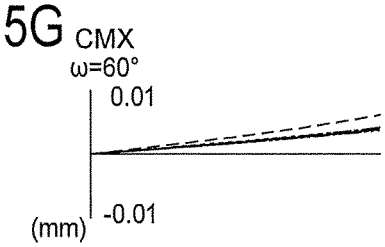
FIG.5G CMX ω=60°
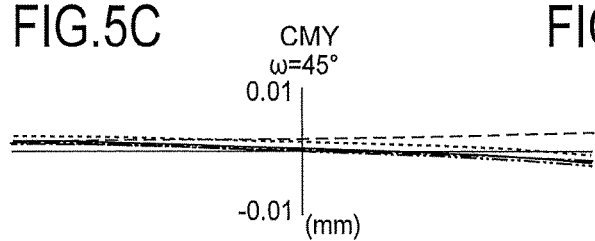
FIG.5C CMY ω=45°
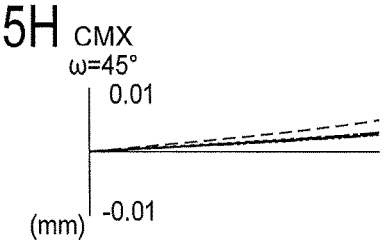
FIG.5H CMX ω=45°
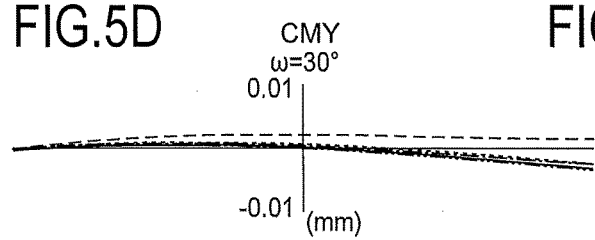
FIG.5D CMY ω=30°
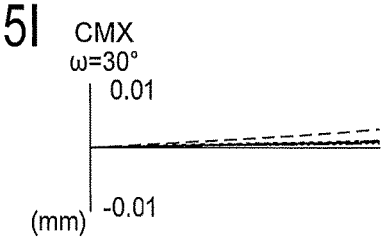
FIG.5I CMX ω=30°
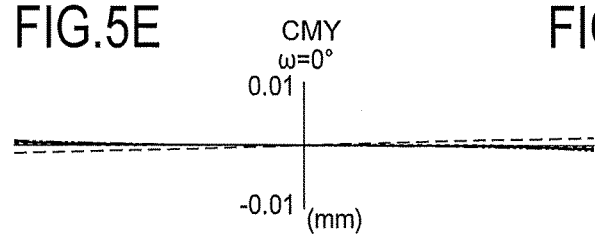
FIG.5E CMY ω=0°
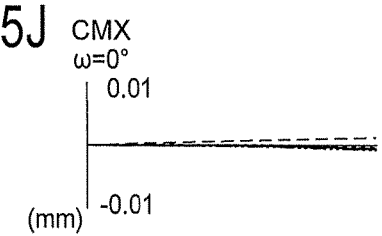
FIG.5J CMX ω=0°
```
---------  656.2700 NM
           587.5600 NM
-·-·-·-·-  546.0700 NM
-··-··-··  486.1000 NM
- - - - -  435.8300 NM
```

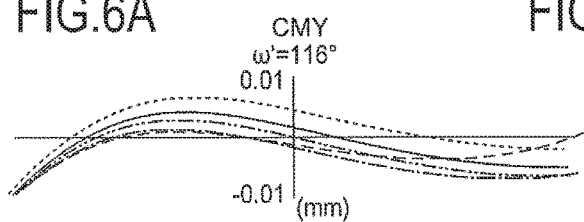
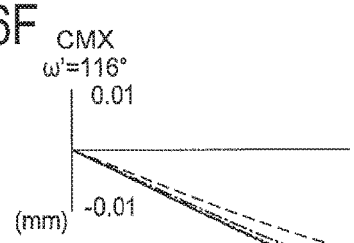
FIG.6A CMY ω'=116°
FIG.6F CMX ω'=116°
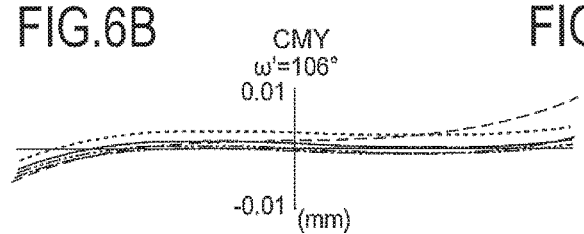
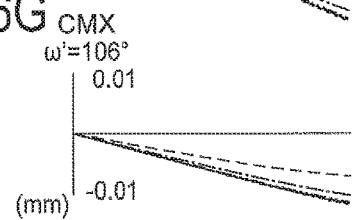
FIG.6B CMY ω'=106°
FIG.6G CMX ω'=106°
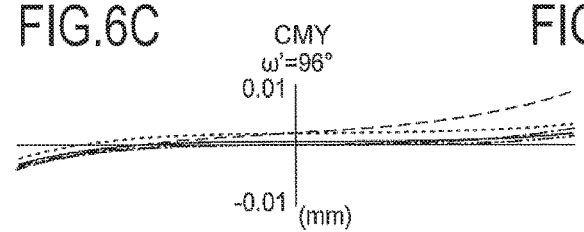
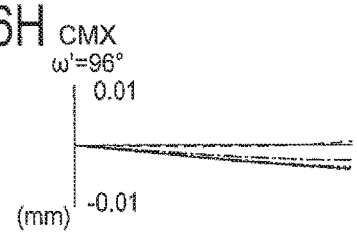
FIG.6C CMY ω'=96°
FIG.6H CMX ω'=96°
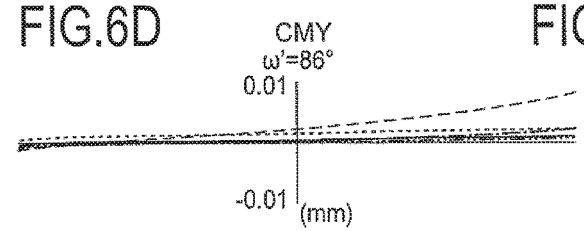
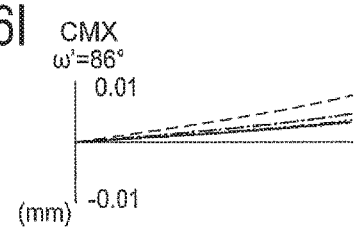
FIG.6D CMY ω'=86°
FIG.6I CMX ω'=86°
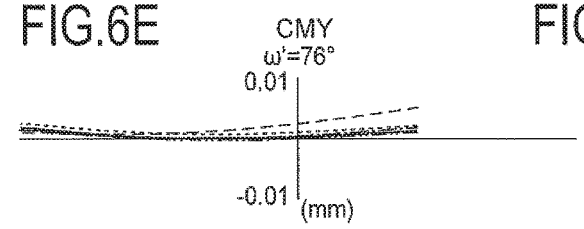
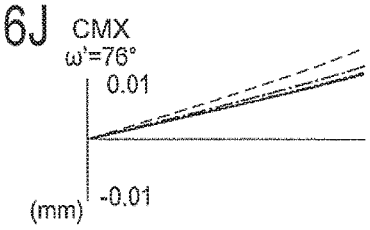
FIG.6E CMY ω'=76°
FIG.6J CMX ω'=76°

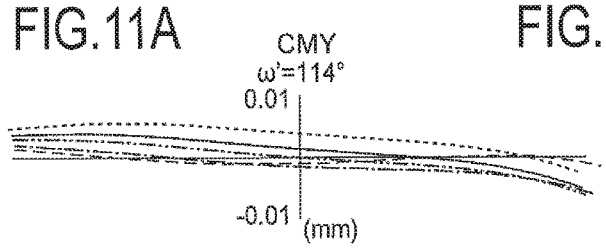
FIG.11A CMY ω'=114°
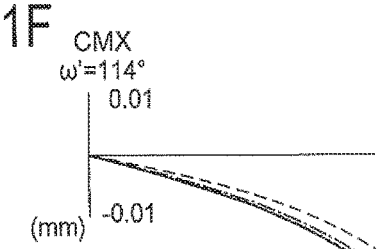
FIG.11F CMX ω'=114°
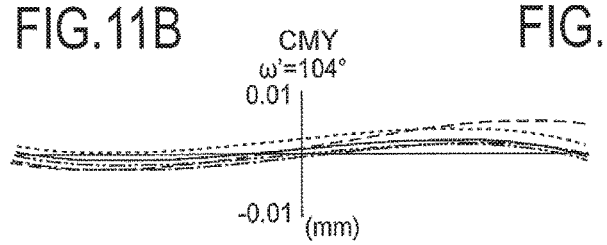
FIG.11B CMY ω'=104°
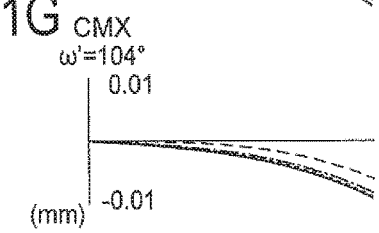
FIG.11G CMX ω'=104°
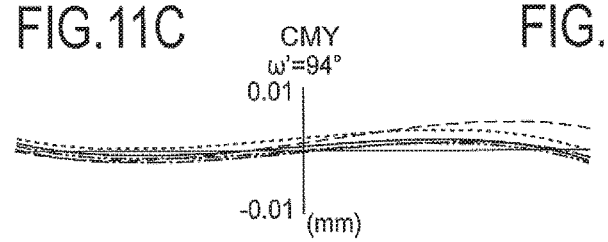
FIG.11C CMY ω'=94°
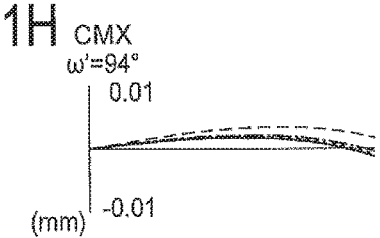
FIG.11H CMX ω'=94°
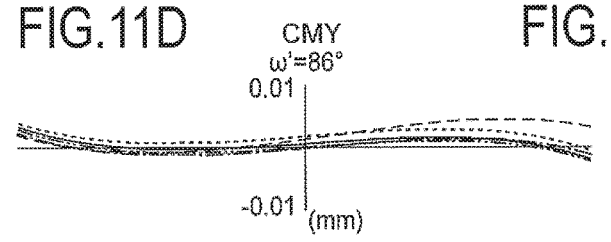
FIG.11D CMY ω'=86°
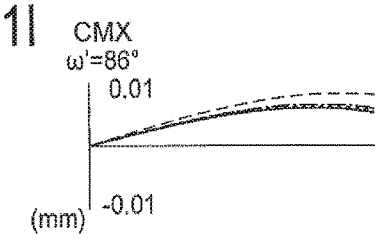
FIG.11I CMX ω'=86°
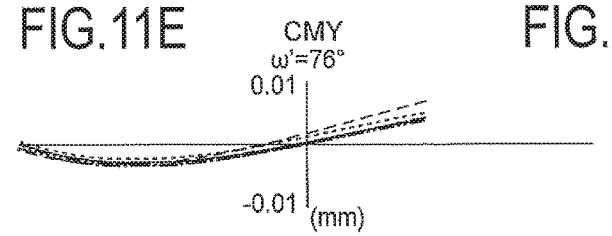
FIG.11E CMY ω'=76°
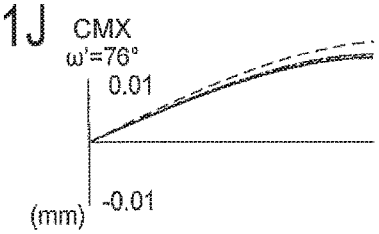
FIG.11J CMX ω'=76°

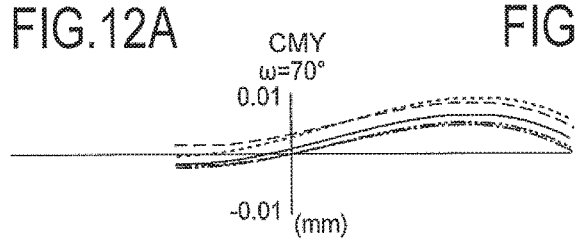
FIG.12A CMY ω=70°
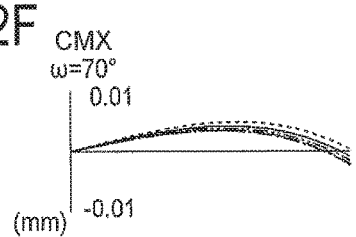
FIG.12F CMX ω=70°
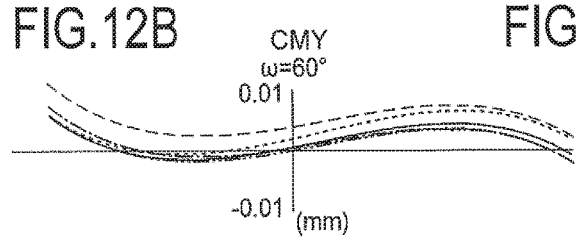
FIG.12B CMY ω=60°
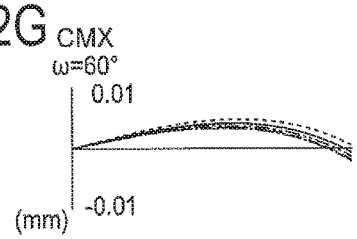
FIG.12G CMX ω=60°
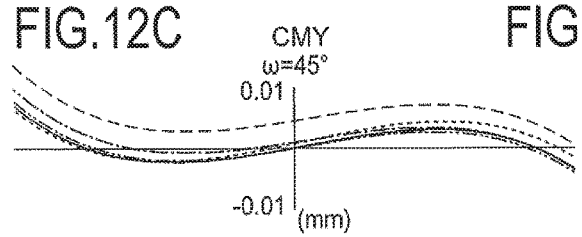
FIG.12C CMY ω=45°
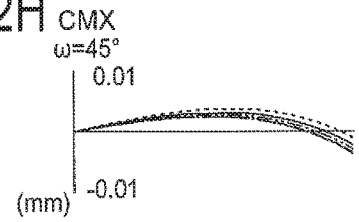
FIG.12H CMX ω=45°
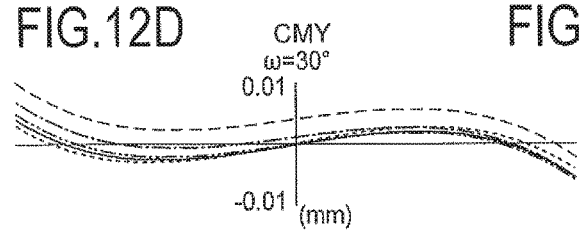
FIG.12D CMY ω=30°
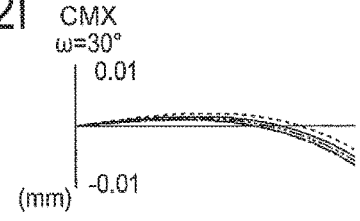
FIG.12I CMX ω=30°
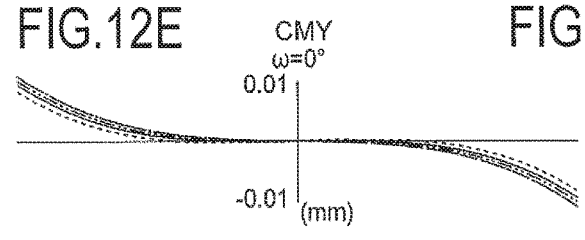
FIG.12E CMY ω=0°
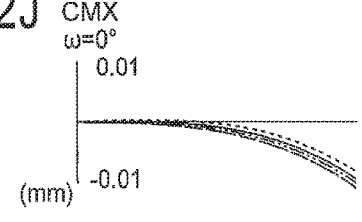
FIG.12J CMX ω=0°

FIG.13A
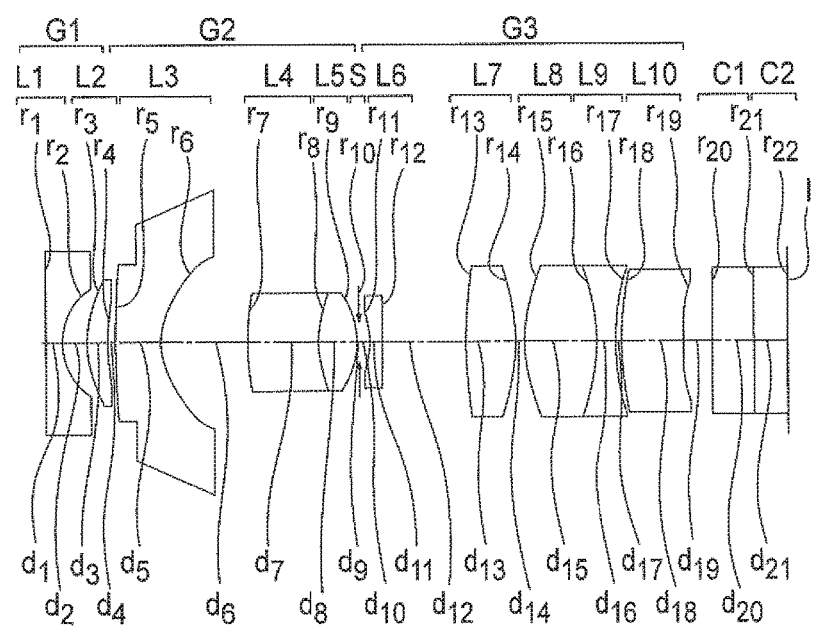
FIG.13B
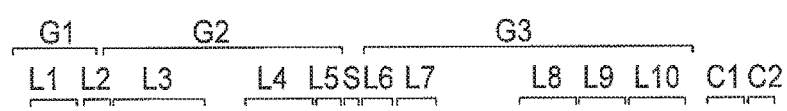
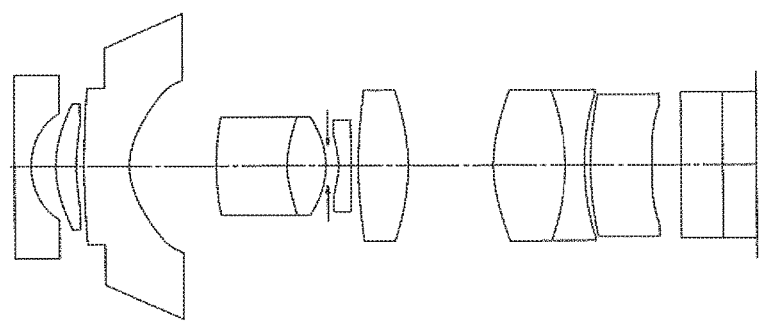

WIDE ANGLE OPTICAL SYSTEM

CROSS-REFERENCE TO RELATED APPLICATION

The present application is a continuation application of PCT/JP2016/067388 filed on Jun. 10, 2016 which is based upon and claims the benefit of priority from Japanese Patent Application No. 2015-121166 filed on Jun. 16, 2015; the entire contents of which are incorporated herein by reference.

BACKGROUND OF THE INVENTION

Field of the Invention

The present invention relates to a wide angle optical system, and particularly to an optical system which enables to observe simultaneously an object in front and an object on a side.

Description of the Related Art

An optical system that enables to observe simultaneously an object in front and an object on a side has been disclosed in Japanese Patent Application Laid-open Publication No. 2008-309861 and Japanese Patent Application Laid-open Publication No. 2011-48086.

The optical system disclosed in Japanese Patent Application Laid-open Publication No. 2008-309861 includes in order from an object side, a front group having a negative refractive power, an aperture stop, and a rear group having a positive refractive power. The front group includes a first lens group having a negative refractive power and a second lens group. The rear group includes a third lens group having a positive refractive power and a fourth lens group having a positive refractive power. The first lens group includes a negative lens or one of a negative lens and a positive lens.

The optical system disclosed in Japanese Patent Application Laid-open Publication No. 2008-309861 has a direct-viewing optical path and a side-viewing optical path. In the direct-viewing optical path, a third transmitting surface and a fourth transmitting surface are disposed. In the side-viewing optical path, a first transmitting surface, a first reflecting surface, a second reflecting surface, and a second transmitting surface are disposed.

The optical system disclosed in Japanese Patent application Laid-open Publication No. 2011-48086 includes in order from an object side a front group and a rear group. The front group includes a first lens group having a negative refractive power and a second lens group. The rear group includes a third lens group having a positive refractive power. The first lens group includes a negative lens.

The optical system disclosed in Japanese Patent Application Laid-open Publication No. 2011-48086 includes a first optical system and a second optical system. The first optical system is for observing an object in front, and includes the first lens group, the second lens group, an aperture stop, and the third lens group. The second optical system is for observing an object on a side and includes the second lens group, the aperture stop, and the third lens group.

In the first optical system, light from the object in front passes through the first transmitting surface and the second transmitting surface. In the second optical system, light from the object on a side passes through a third surface, a second reflecting surface, a first reflecting surface, and a second transmitting surface.

SUMMARY OF THE INVENTION

A wide angle optical system according to the present invention comprises:

a first optical path along which light from an object in front passes, a second optical path along which light from an object on a side passes, and a common optical path along which the light from the object in front and the light from the object on a side pass, wherein the wide angle optical system includes in order from a side of the object in front, a first lens group having a negative refractive power, a second lens group having a catadioptric optical element, an aperture stop, and a third lens group having a positive refractive power, and the first lens group includes a positive lens and a negative lens, and the catadioptric optical element has a first surface, a second surface, and a third surface that is formed between the first surface and the second surface, and the first surface has a first transmitting surface and a first reflecting surface, and the first transmitting surface is formed to include an optical axis of the first optical path, and the first reflecting surface is an annular reflecting surface, and is formed around the first transmitting surface, and the second surface has a second transmitting surface and a second reflecting surface, and the second transmitting surface is formed to include the optical axis of the first optical path, and the second reflecting surface is an annular reflecting surface, and is formed around the second transmitting surface, and the third surface has a third transmitting surface, and the third transmitting surface is a side surface of a circular truncated cone, and an apex of the circular truncated cone is positioned on the side of the object in front of the first lens group, and in the first optical path, the first lens group, the first transmitting surface, and the second transmitting surface are positioned in order from the side of the object in front, and in the second optical path, the third transmitting surface, the second reflecting surface, the first reflecting surface, and the second transmitting surface are positioned in order from the side of the object on a side, and the aperture stop and the third lens group are positioned in the common optical path, and the following conditional expressions (1), (2), and (3) are satisfied:

$$\nu p < \nu n \quad (1),$$

$$|\phi p| < |\phi n| \quad (2), \text{ and}$$

$$90° - \theta k < \alpha/2 \quad (3)$$

where, $\nu p$ denotes Abbe number for the positive lens, $\nu n$ denotes Abbe number for the negative lens, $\phi p$ denotes a refractive power of the positive lens, φn denotes a refractive power of the negative lens, θk denotes the minimum half angle of view for the second optical path, and 0°<θk<90°, and α denotes an apex angle of the circular truncated cone.

BRIEF DESCRIPTION OF THE DRAWINGS

FIG. 1A and FIG. 1B are diagrams showing a wide angle optical system of a single focal length type according to the present embodiment, where, FIG. 1A is a diagram showing a schematic arrangement of the overall optical system and FIG. 1B is a diagram showing a detail arrangement of a catadioptric optical element;

FIG. 3A and FIG. 3B are cross-sectional views showing an arrangement of a wide angle optical system of a variable magnification type according to the present embodiment, where, FIG. 3A is a cross-sectional view of an arrangement at a wide angle end and FIG. 3B is a cross-sectional view of an arrangement at a telephoto end;

FIG. 4A is a cross-sectional view of an arrangement of a first optical system and FIG. 4B is a cross-sectional view of an arrangement of a second optical system;

FIG. 5A, FIG. 5B, FIG. 5C, FIG. 5D, FIG. 5E, FIG. 5F, FIG. 5G, FIG. 5H, FIG. 5I, and FIG. 5J (hereinafter, 'FIG. 5A to FIG. 5J') are aberration diagrams for the first optical system of the wide angle optical system according to the example 1, where, FIG. 5A, FIG. 5B, FIG. 5C, FIG. 5D, and FIG. 5E show a coma and a chromatic aberration of magnification for a meridional plane, and FIG. 5F, FIG. 5G, FIG. 5H, FIG. 5I, and FIG. 5J show a coma and a chromatic aberration of magnification for a sagittal plane;

FIG. 6A, FIG. 6B, FIG. 6C, FIG. 6D, FIG. 6E, FIG. 6F, FIG. 6G, FIG. 6H, FIG. 6I, FIG. 6J (hereinafter, 'FIG. 6A to FIG. 6J') are aberration diagrams for the second optical system of the wide angle optical system according to the example 1, where, FIG. 6A, FIG. 6B, FIG. 6C, FIG. 6D, and FIG. 6E show a coma and a chromatic aberration of magnification for a meridional plane, and FIG. 6F, FIG. 6G, FIG. 6H, FIG. 6I, and FIG. 6J show a coma and a chromatic aberration of magnification for a sagittal plane;

FIG. 7A is a cross-sectional view of an arrangement at a wide angle end and FIG. 7B is a cross-sectional view of an arrangement at a telephoto end;

FIG. 8A, FIG. 8B, FIG. 8C, FIG. 8D, and FIG. 8E show a coma aberration and a chromatic aberration of magnification for a meridional plane, and FIG. 8F, FIG. 8G, FIG. 8H, FIG. 8I, and FIG. 8J show a coma and a chromatic aberration of magnification for a sagittal plane;

FIG. 9A is a cross-sectional view of an arrangement at a wide angle end and FIG. 9B is a cross-sectional view of an arrangement at a telephoto end;

FIG. 10A, FIG. 10B, FIG. 10C, FIG. 10D, and FIG. 10E show a coma and a chromatic aberration of magnification for a meridional plane, and FIG. 10F, FIG. 10G, FIG. 10H, FIG. 10I, and FIG. 10J show a coma and a chromatic aberration of magnification for a sagittal plane;

FIG. 11A, FIG. 11B, FIG. 11C, FIG. 11D, FIG. 11E, FIG. 11F, FIG. 11G, FIG. 11H, FIG. 11I, and FIG. 11J (hereinafter, 'FIG. 11A to FIG. 11J') are aberration diagrams for a second optical system, at the wide angle end of the wide angle optical system according to the example 3, where, FIG. 11A, FIG. 11B, FIG. 11C, FIG. 11D, and FIG. 11E show a coma and a chromatic aberration of magnification for a meridional plane, and FIG. 11F, FIG. 11G, FIG. 11H, FIG. 11I, and FIG. 11J show a coma and a chromatic aberration of magnification for a sagittal plane;

FIG. 12A, FIG. 12B, FIG. 12C, FIG. 12D, FIG. 12E, FIG. 12F, FIG. 12G, FIG. 12H, FIG. 12I, and FIG. 12J (hereinafter, 'FIG. 12A to FIG. 12J') are aberration diagrams for the first optical system, at a telephoto end of the wide angle optical system according to the example 3, where, FIG. 12A, FIG. 12B, FIG. 12C, FIG. 12D, and FIG. 12E show a coma and a chromatic aberration of magnification for a meridional plane, and FIG. 12F, FIG. 12G, FIG. 12H, FIG. 12I, and FIG. 12J show a coma and a chromatic aberration of magnification for a sagittal plane;

FIG. 13A and FIG. 13B are cross-sectional views showing an arrangement of a wide angle optical system according to an example 4, where, FIG. 13A is a cross-sectional view of an arrangement at a wide angle end and FIG. 13B is a cross-sectional view of an arrangement at a telephoto end;

FIG. 14A, FIG. 14B, FIG. 14C, FIG. 14O, and FIG. 14E show a coma and a chromatic aberration of magnification for a meridional plane, and FIG. 14F, FIG. 14G, FIG. 14H, FIG. 14I, and FIG. 14J show a coma and a chromatic aberration of magnification for a sagittal plane;

FIG. 15A, FIG. 15B, FIG. 15C, FIG. 15D, FIG. 15E, FIG. 15F, FIG. 15G, FIG. 15H, FIG. 15I, and FIG. 15J (hereinafter, 'FIG. 15A to FIG. 15J') are aberration diagrams for a second optical system, at the wide angle end of the wide angle optical system according to the example 4, where, FIG. 15A, FIG. 15B, FIG. 15C, FIG. 15D, and FIG. 15E show a coma and a chromatic aberration of magnification for a meridional plane, and FIG. 15F, FIG. 15G, FIG. 15H, FIG. 15I, and FIG. 15J show a coma and a chromatic aberration of magnification for a sagittal plane; FIG. 16A, FIG. 16B, FIG. 16O, FIG. 16D, and FIG. 16E show a coma and a chromatic aberration of magnification for a meridional plane, and FIG. 16F, FIG. 16G, FIG. 16H, FIG. 16I, and FIG. 16J show a coma and a chromatic aberration of magnification for a sagittal plane.

DETAILED DESCRIPTION OF THE INVENTION

Figure 2:
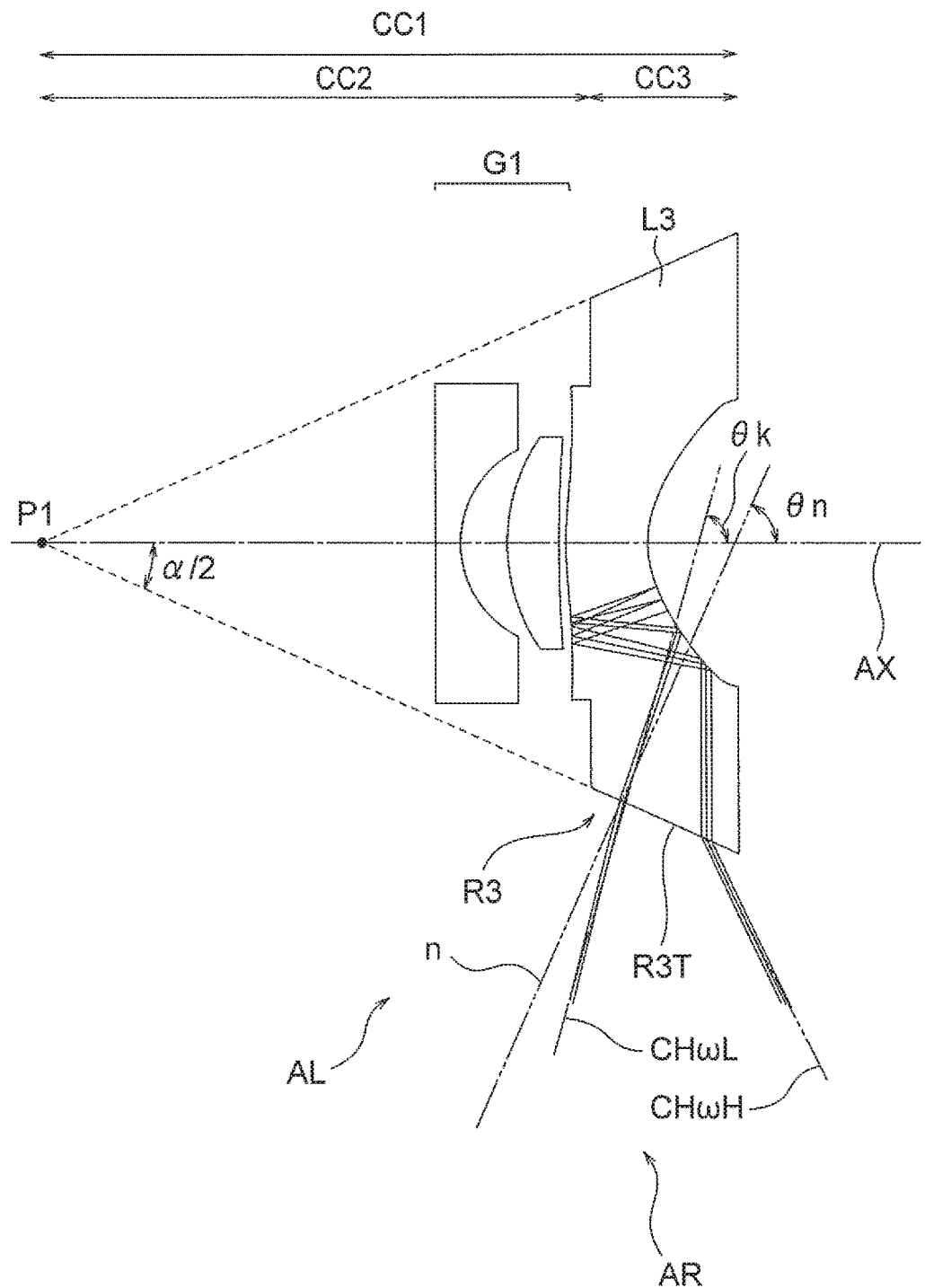
FIG. 2 is a diagram showing light beams incident on a third transmitting surface.

Reasons for adopting such arrangements and effects thereof in a wide angle optical system according to the present embodiment will be described below by referring to the accompanying diagrams. However, the present invention is not limited to the following endoscope objective optical system according to the present embodiments.

A wide angle optical system according to the an embodiment includes a first optical path along which light from an object in front passes, a second optical path along which light from an object on a side passes, and a common optical path along which the light from the object in front and the light from the object on a side pass, wherein, the wide angle optical system includes in order from a side of the object in front, a first lens group having a negative refractive power, a second lens group having a catadioptric optical element, an aperture stop, and a third lens group having a positive refractive power, and the first lens group includes a positive lens and a negative lens, and the catadioptric optical element has a first surface, a second surface, and a third surface that is formed between the first surface and the second surface, and the first surface has a first transmitting surface and a first reflecting surface, and the first transmitting surface is formed to include an optical axis of the first optical path, and the first reflecting surface is an annular-shape reflecting surface, and is formed around the first transmitting surface, and the second surface has a second transmitting surface and a second reflecting surface, and the second transmitting surface is formed to include the optical axis of the first optical path, and the second reflecting surface is an annular reflecting surface, and is formed around the second transmitting surface, and the third surface has a third transmitting surface, and the third transmitting surface is a side surface of a circular truncated cone, and an apex of the circular truncated cone is positioned on the side of the object in front of the first lens group, and in the first optical path, the first lens group, the first transmitting surface, and the second transmitting surface are positioned in order from the side of the object in front, and in the second optical path, the third transmitting surface, the second reflecting surface, the first reflecting surface, and the second transmitting surface are positioned in order from the side of the object on a side, and the aperture stop and the third lens group are positioned in the common optical path, and the following conditional expressions (1), (2), and (3) are satisfied:

$$\upsilon p < \upsilon n \quad (1),$$

$$|\phi p| < |\phi n| \quad (2), \text{ and}$$

$$90° - \theta k < \alpha/2 \quad (3)$$

where, $\upsilon p$ denotes Abbe number for the positive lens,
$\upsilon n$ denotes Abbe number for the negative lens,
$\phi p$ denotes a refractive power of the positive lens,
$\phi n$ denotes a refractive power of the negative lens,
$\theta k$ denotes the minimum half angle of view for the second optical path, and $0° < \theta k < 90°$, and
$\alpha$ denotes an apex angle of the circular truncated cone.

The wide angle optical system according to the present embodiment will be described below. FIG. 1A and FIG. 1B are diagrams showing a wide angle optical system of a single focal length type according to the present embodiment, where, FIG. 1A is a diagram showing a schematic arrangement of the overall optical system and FIG. 1B is a diagram showing a detail arrangement of catadioptric optical element.

As shown in FIG. 1A, the wide angle optical system of the present embodiment has a first optical path OP1 along which light from an object in front passes, a second optical path OP2 along which light from an object on a side passes, and a common optical path OP3 along which the light from the object in front and the light from the object on a side pass.

Moreover, the wide angle optical system of the present embodiment includes in order from a side of the object in front, a first lens group G1 having a negative refractive power, a second lens group G2, an aperture stop S, and a third lens group G3 having a positive refractive power.

The first lens group G1 includes a negative lens L1 and a positive lens L2.

The second lens group G2 includes a catadioptric optical element L3. The second lens group G2 further includes a positive lens L4.

The third lens group G3 includes a positive lens L5, a negative lens L6, a negative lens L7, a positive lens L8, a negative lens L9, and a positive lens L10. Here, a cemented lens CL1 is formed by the positive lens L5 and the negative lens L6. Moreover, a cemented lens CL2 is formed by the positive lens L8 and the negative lens L9.

As shown in FIG. 1B, the catadioptric optical element L3 has a first surface R1, a second surface R2, and a third surface R3. The third surface R3 is formed between the first surface R1 and the second surface R2.

The first surface R1 has a first transmitting surface R1T and a first reflecting surface R1R. The first transmitting surface R1T is formed to include an optical axis of the first optical path OP1. The first reflecting surface R1R is an annular reflecting surface and is formed around the first transmitting surface R1T.

The second surface R2 has a second transmitting surface R2T and a second reflecting surface R2R. The second transmitting surface R2T is formed to include the optical axis of the first optical path OP1. The second reflecting surface R2R is an annular reflecting surface, and is formed around the second transmitting surface R2T.

The third surface R3 has a third transmitting surface R3T. The third transmitting surface R3T is a side surface of a circular truncated cone. An apex of the circular truncated cone is positioned on the side of the object in front, of the first lens group G1.

In the first optical path OP1, the first lens group G1, the first transmitting surface R1T, and the second transmitting surface R2T are positioned in order from the side of the object in front. In the second optical path OP2, the third transmitting surface R3T, the second reflecting surface R2R, the first reflecting surface R1R, and the second transmitting surface R2T are positioned in order from the side of the object on a side. The aperture stop S and the third lens group G3 are positioned in the common optical path OP3.

In the wide angle optical system of the present embodiment, a light beam advancing along the first optical path OP1 passes through the first lens group G1, the first transmitting surface R1T and the second transmitting surface R2T. Whereas, a light beam advancing along the second optical path OP2 does not pass through the first lens group G1. Therefore, in the wide angle optical system of the present embodiment, the number of refracting surfaces in the first optical path OP1 is larger than the number of refracting surfaces in the second optical path OP2.

Here, in the wide angle optical system according to the present embodiment, the first lens group G1 includes the positive lens L2 in addition to the negative lens L1. Therefore, by the negative lens L1 and the positive lens L2, it is possible to control an amount and a direction of a chromatic aberration of magnification that occurs.

Here, it is preferable that the following conditional expressions (1) and (2) be satisfied:

$$\nu p < \nu n \quad (1), \text{ and}$$

$$|\phi p| < |\phi n| \quad (2), \text{ and}$$

where,
νp denotes Abbe number for the positive lens,
νn denotes Abbe number for the negative lens,
φp denotes a refractive power of the positive lens, and
φn denotes a refractive power of the negative lens.

When conditional expression (1) is not satisfied, Abbe number for the positive lens becomes higher than Abbe number for the negative lens. In this case, it becomes difficult to make small the amount of the chromatic aberration of magnification that occurs in the first optical path OP1.

When conditional expression (2) is not satisfied, the refractive power of the positive lens becomes large. In this case, since a negative refractive power cannot be imparted to the first lens group, a wide angle of view cannot be secured.

Furthermore, it is preferable that the following conditional expression (3) be satisfied:

$$90° - \theta k < \alpha/2 \quad (3)$$

where,
θk denotes the minimum half angle of view for the second optical path, and 0°<θk<90°, and
α denotes an apex angle of the circular truncated cone.

Conditional expression (3) is a conditional expression related to a light beam incident on the third transmitting surface R3T. FIG. 2 is a diagram showing light beams incident on the third transmitting surface R3T. A surface shape of the third transmitting surface R3T is same as that of a side surface of a circular truncated cone CC3. As shown in FIG. 2, the circular truncated cone CC3 is a portion remained after removing a small circular cone CC2 from a circular cone CC1. Therefore, an apex of the circular cone CC1 before removing the small circular cone CC2 is to be deemed as an apex of the circular truncated cone CC3.

In the wide angle optical system according to the present embodiment, an apex P1 of the circular truncated cone CC3 is positioned on the side of the object in front of the first lens group G1 as shown in FIG. 2. Therefore, in the wide angle optical system of the present embodiment, a normal n of the third transmitting surface R3T is not orthogonal to an optical axis AX. In FIG. 2, an angle made by the normal n and the optical axis AX is indicated by θn.

In the second optical path, light beams from the object on a side are incident on the third transmitting surface R3T at various angles. A light beam having a principal ray CHωL and a light beam having a principal ray CHωH are shown in FIG. 2. When an angle made by a principal ray of a light beam incident on the third transmitting surface R3T and the optical axis AX is let to be a half angle of view, the half angle of view is minimum for the light beam having the principal ray CHωL and is maximum for the light beam having the principal ray CHωH.

Conditional expression (3) can be deformed as follows.

$$90° - \alpha/2 < \theta k$$

Here, since 90°−α/2=θn, the expression (3) becomes as follows.

$$\theta n < \theta k$$

Since θk is the minimum half angle of view in the second optical path, in FIG. 2, an angle made by the principal ray CHωL and the optical axis AX becomes θk. When θn and θK are compared, θn<θk in FIG. 2. In a state in which θn<θk is satisfied, the light beam with the principal ray CHωL is incident on the third transmitting surface R3T from an area on a right side of the normal n (hereinafter, referred to as 'area AR'). Furthermore, even a light ray having an angle of view larger than θk is also incident on the third transmitting surface R3T from the area AR.

Thus, when θn<θk is satisfied, or in other words, when conditional expression (3) is satisfied, all the light beams from the object on a side are incident on the third transmitting surface R3T from the area AR.

Whereas, in a state when θn<θk is not satisfied, which is not shown in the diagram, the light beam with the principal ray CHωL is incident on the third transmitting surface R3T from an area on a left side of the normal n (hereinafter, referred to as 'area AL'). The normal n is also included in the area AL.

Therefore, when condition θn<θk is not satisfied, or in other words, when conditional expression (3) is not satisfied, at least some of the beams are incident on the third transmitting surface R3T from the area AL.

Regarding a sign (plus and minus) of the angle of incidence, the sign is let to be plus when the light beam is incident on the third transmitting surface R3T from the area AR and minus when the light beam is incident on the third transmitting surface R3T from the area AL. When conditional expression (3) is satisfied, since all the beams are incident on the third transmitting surface R3T from the area AR, the sign of the angle of incidence for all the light beams becomes plus. As a result, the direction of the chromatic aberration of magnification that occurs in the second optical path is the same direction for all the angles of view. In other words, the amount of the chromatic aberration of magnification that occurs in the second optical path is either a positive amount or a negative amount for all the angles of view.

As mentioned above, since the first lens group G1 includes the negative lens L1 and the positive lens L2, it is possible to control the amount and the direction of the chromatic aberration of magnification that occurs in the first optical path. For instance, it is possible to let the direction of the chromatic aberration of magnification that occurs in the first optical path to be the same direction for all the angles of view. Furthermore, it is possible to let the direction of the chromatic aberration of magnification that occurs in the first optical path to be identical with the direction of the chromatic aberration of magnification that occurs in the second optical path.

When the direction of the chromatic aberration of magnification in the first optical path and the direction of the chromatic aberration of magnification in the second optical path are identical, since the chromatic aberration of magnification occurred in the same direction may correct in the third lens group, correction of the chromatic aberration of magnification in the third lens group becomes easy. As a result, in the wide angle optical system according to the present embodiment, it is possible to correct the chromatic aberration of magnification favorably in the overall optical system.

When conditional expression (3) is not satisfied, since some of the light beams are incident on the third transmitting surface R3T from the area AL, the angle of incidence becomes negative for at least some of the light beams and positive for the rest of the light beams. In this case, the direction of the chromatic aberration of magnification that occurs is not same for all the angles of view. In other words, the amount of the chromatic aberration that occurs becomes negative for some of the angles of view, and becomes positive for the rest of the angles of view.

If it is only the second optical path, it is possible to correct the chromatic aberration of magnification in the third lens group. However, as mentioned above, the chromatic aberration of magnification in the first optical path has to be corrected in the third lens group. For such reason, it becomes difficult to correct favorably the chromatic aberration of magnification occurred in the second optical path. As a result, it is not possible to correct the chromatic aberration of magnification in the overall optical system favorably.

In the wide angle optical system according to the present embodiment, it is preferable that the following conditional expression (4) be satisfied:

$$0.7<(|\phi n|/\upsilon n)/(\phi p/\upsilon p)<1.5 \quad (4)$$

where,
υp denotes Abbe number for the positive lens
υn denotes Abbe number for the negative lens,
φp denotes the refractive power of the positive lens, and
φn denotes the refractive power of the negative lens.

Each of $|\phi n|/\upsilon n$ and $\phi p/\upsilon p$ indicates a degree of an achromatic effect or a degree of a color-out effect. When a value of $|\phi n|/\upsilon n$ and a value of $\phi p/\upsilon p$ becomes large, am amount of a chromatic aberration that occurs becomes large.

In a case of falling below a lower limit value of conditional expression (4), since an effect of chromatic dispersion due to the positive lens becomes excessively strong, correction of the chromatic aberration of magnification becomes difficult. In a case of exceeding an upper limit value of conditional expression (4), the effect of chromatic dispersion due to the positive lens is weakened and an effect of chromatic dispersion due to the negative lens becomes strong. As a result, correction of the chromatic aberration of magnification becomes difficult.

Moreover, in the wide angle optical system according to the present embodiment, it is preferable that the following conditional expressions (5) and (6) be satisfied:

$$35<\upsilon n \quad (5), \text{ and}$$

$$\upsilon p<35 \quad (6)$$

where,
υp denotes Abbe number for the positive lens, and
υn denotes Abbe number for the negative lens.

In the wide angle optical system according to the present embodiment, an optical system of a retro-focus type is adopted. Therefore, it is desirable that the negative lens in the first lens group has a large refractive power. By satisfying conditional expressions (5) and (6), it is possible to select a glass material having a higher refractive index for the positive lens and a glass material with a smaller chromatic dispersion for the negative lens. As a result, it is possible to correct the chromatic aberration of magnification efficiently.

Moreover, in the wide angle optical system according to the present embodiment, it is preferable that the third lens group include a lens that moves along an optical axis.

By making such arrangement, it is possible to change the angle of view. FIG. 3A and FIG. 3B are cross-sectional views showing an arrangement of a variable magnification optical system according to the present embodiment, where, FIG. 3A is a cross-sectional view of an arrangement at a wide angle end and FIG. 3B is a cross-sectional view of an arrangement at a telephoto end.

Same reference numerals are used for components same as in FIG. 1A, and description thereof is omitted. The wide angle optical system shown in FIG. 3A and FIG. 3B is an optical system in which a movement of the cemented lens CL1 in the optical axial direction in the wide angle optical system shown in FIG. 1A and FIG. 1B is made possible.

At the time of zooming from the wide angle end to the telephoto end, the cemented lens CL1 moves to come closer to the second lens group G2. Accordingly, it is possible to carry out observation of an object on a side and an object in front at the wide angle end, and observation of only the object in front at the telephoto end.

Moreover, by zooming from the wide angle end to the telephoto end, in the observation of the object in front, a distance up to a near object becomes shorter at the telephoto end than at the wide angle end. Therefore, a site of lesion discovered by a wide angle observation can be observed more closely, in a larger size. The near object refers to an object that is positioned nearest to the optical system.

The lens to be moved is not restricted to a cemented lens. The lens to be moved may include a single lens. Moreover, the number of lenses to be moved is not restricted to one. A plurality of lenses may be moved. Furthermore, a direction of movement is not restricted to the direction toward the second lens group G2. At the time of zooming from the wide angle end to the telephoto end, the movement may be in a direction of moving away from the second lens group G2.

Moreover, in the wide angle optical system according to the present embodiment, it is preferable that a lens nearest to image in the third lens group be fixed.

When the lens nearest to image in the third lens group is moved, a back focus varies. Therefore, it is not desirable to move the lens nearest to image in the third lens group.

In the wide angle optical system according to the present embodiment, it is preferable that the following conditional expression (7) be satisfied.

$$0.7<|f3/fi|<1.2 \quad (7)$$

where,
f3 denotes a focal length of the third lens group at a wide angle end, and
fi denotes a focal length of the lens that moves in the optical axial direction.

In a case of falling below a lower limit value of conditional expression (7), the focal length of the lens that moves becomes long. As a result, it becomes difficult to change the angle of view substantially. In a case of exceeding an upper limit value of conditional expression (7), a change in the angle of view and a variation in a focal position become excessively large.

Moreover, in the wide angle optical system according to the present embodiment, it is preferable that switching to the observation of the object in front and the object on a side and the observation of the object in front only be possible by a movable lens that moves along the optical axial direction.

By making such arrangement, it is possible to observe different ranges.

Examples according to the present invention will be described below. An example 1 is a wide angle optical system of a single focal length type, and examples from an example 2 to an example 4 are a wide angle optical system of a variable magnification type. The wide angle optical system according to the example 1 includes a first optical system and a second optical system. The wide angle optical systems according to the examples from the example 2 to the example 4 have different arrangements at a wide angle end and a telephoto end. At the wide angle end, the wide angle optical system includes a first optical system and a second optical system. At the telephoto end, the wide angle optical system includes a first optical system only.

The first optical system is an optical system for observing the object in front, and has a first optical path and a common optical path. The second optical system is an optical system for observing the object on a side, and has a second optical path and a common optical path. The object in front is positioned in a direction along an optical axis of the first optical path. The object on a side is positioned in a direction substantially orthogonal to the optical axis of the first optical path.

In aberration diagrams of each example, aberration diagrams on a left side show a coma and a chromatic aberration of magnification for a meridional plane and aberration diagrams on a right side show a coma and a chromatic aberration of magnification for a sagittal plane. Moreover, a vertical axis indicates an amount of aberration and a horizontal axis indicates brightness. The unit of the amount of aberration is mm. Moreover, ω denotes a half angle of view for the first optical system and ω' denotes a half angle of view for the second optical system. The unit of both ω and ω' is °, and the unit of wavelength of an aberration curve is nm.

EXAMPLE 1

Figure 4A:
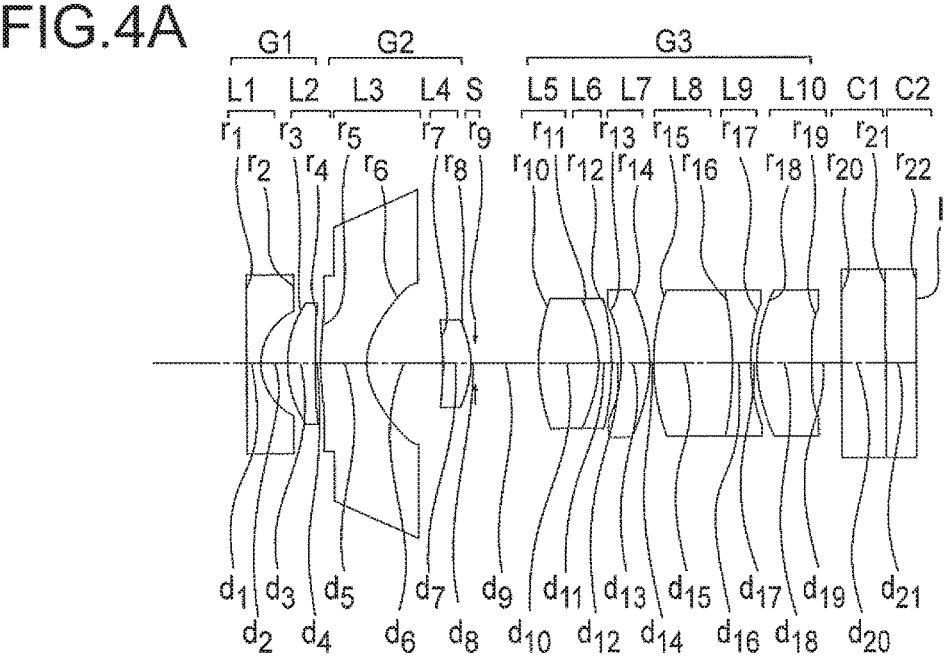
FIG. 4A and FIG. 4B are cross-sectional views showing an arrangement of a wide angle optical system according to an example 1, where.
Figure 4B:
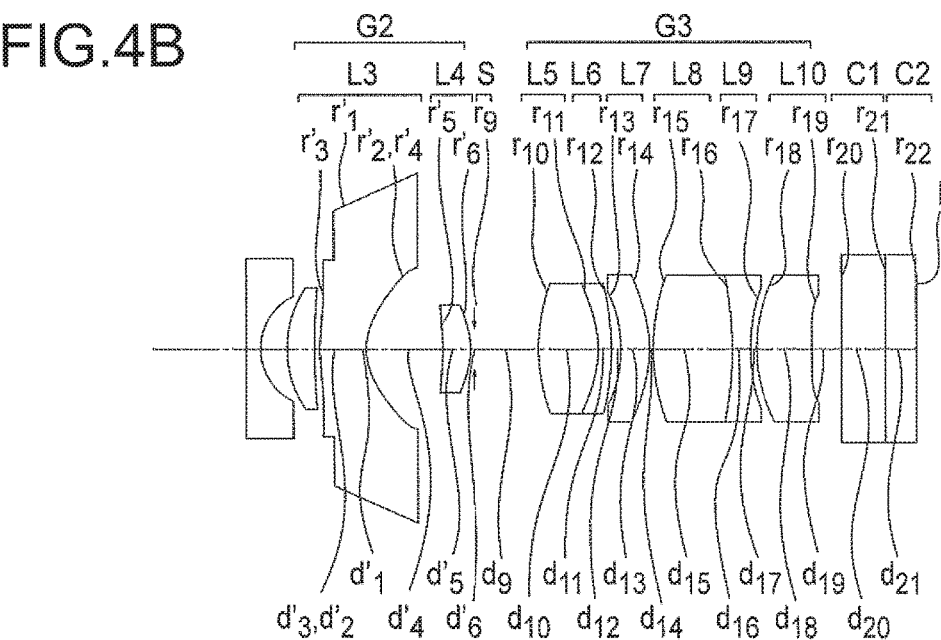

The wide angle optical system according to the example 1 will be described below. FIG. 4A and FIG. 4B are cross-sectional views showing an arrangement of the wide angle optical system according to the example 1, where, FIG. 4A is a cross-sectional view of an arrangement of the first optical system and FIG. 4B is a cross-sectional view of an arrangement of the second optical system.

In the cross-sectional view of the arrangement of the second optical system, an optical surface in a second lens group is denoted by r' and a distance is denoted by d'. An aperture stop and a third lens group are common in the first optical system and the second optical system. Therefore, for the aperture stop and the third lens group, surfaces r9 to r22 and distances d8 to d21 to are used in the cross-sectional view of the first optical system.

FIG. 5A to FIG. 5J are aberration diagrams for the first optical system of the wide angle optical system according to the example 1. In FIG. 5A and FIG. 5F, ω=71°, in FIG. 5B and FIG. 5G, ω=60°, in FIG. 5C and FIG. 5H, ω=45', in FIG. 5D and FIG. 5I, ω=30°, and in FIG. 5E and FIG. 5J, ω=0°.

FIG. 6A to FIG. 6J are aberration diagrams for the second optical system of the wide angle optical system according to the example 1. In FIG. 6A and FIG. 6F, ω'=116°, in FIG. 6B and FIG. 6G, ω'=106°, in FIG. 6C and FIG. 63, ω=96', in FIG. 6D and FIG. 6I, ω'=86°, and in FIG. 6E and FIG. 6J, ω'=76°.

The wide angle optical system according to the example 1, as shown in FIG. 4A, includes in order from a side of the object in front, a first lens group G1 having a negative refractive power, a second lens group G2, an aperture stop S, and a third lens group G3 having a positive refractive power.

The first lens group G1 includes a planoconcave negative lens L1 of which an object side is a flat surface and a positive meniscus lens L2 having a convex surface directed toward an object side.

The second lens group G2 includes a catadioptric optical element L3 and a positive meniscus lens L4 having a convex surface directed toward an image side.

The third lens group G3 includes a biconvex positive lens L5, a negative meniscus lens L6 having a convex surface directed toward the image side, a negative meniscus lens L7 having a convex surface directed toward the image side, a biconvex positive lens L8, a biconcave negative lens L9, and a positive meniscus lens L10 having a convex surface directed toward the object side. Here, the biconvex positive lens L5 and the negative meniscus lens L6 are cemented. Moreover, the biconvex positive lens L8 and the biconcave negative lens L9 are cemented.

A cover glass C1 and a cover glass C2 are disposed on the image side of the third lens group G3. The cover glass C2 is a cover glass of an image pickup element. An image of the object in front and an image of the object on a side are formed on an image-side surface of the cover glass 2. Therefore, an image pickup surface of the image pickup element is positioned on the image-side surface of the cover glass C2.

An aspheric surface is provided to a total of three surfaces namely, both surfaces of the catadioptric optical element L3 and an image-side surface of the positive meniscus lens L10.

The catadioptric optical element L3 has a first surface, a second surface, and a third surface. The first surface is a surface toward the first lens group G1. The second surface is a surface toward the third lens group G3. The third surface is formed between the first surface and the second surface.

The first surface has a first transmitting surface and a first reflecting surface. The first transmitting surface is formed to include an optical axis of the first optical path. The first reflecting surface is an annular reflecting surface, and is formed around the first transmitting surface.

The second surface has a second transmitting surface and a second reflecting surface. The second transmitting surface is formed to include the optical axis of the first optical path. The second reflecting surface is an annular reflecting surface, and is formed around the second transmitting surface.

The third surface has a third transmitting surface. The third transmitting surface is a side surface of a circular truncated cone. An apex of the circular truncated cone is positioned on the side of the object in front, of the first lens group G1.

In the first optical path, the first lens group, the first transmitting surface, and the second transmitting surface are positioned in order from the side of the object in front. Since both the first surface and the second surface have a convex surface directed toward the object side, in the first optical path, the catadioptric optical element L3 functions as a negative meniscus lens.

In the second optical path, the third transmitting surface, the second reflecting surface, the first reflecting surface, and the second transmitting surface are positioned in order from the side of the object on a side. The third transmitting surface is a flat surface, the second reflecting surface is a reflecting surface which is convex toward the object side, the first reflecting surface is a reflecting surface which is convex toward the image side, and the second transmitting surface is a transmitting surface which is convex toward the object side.

The aperture stop S and the third lens group G3 are positioned in the common optical path.

EXAMPLE 2

Figure 7A:
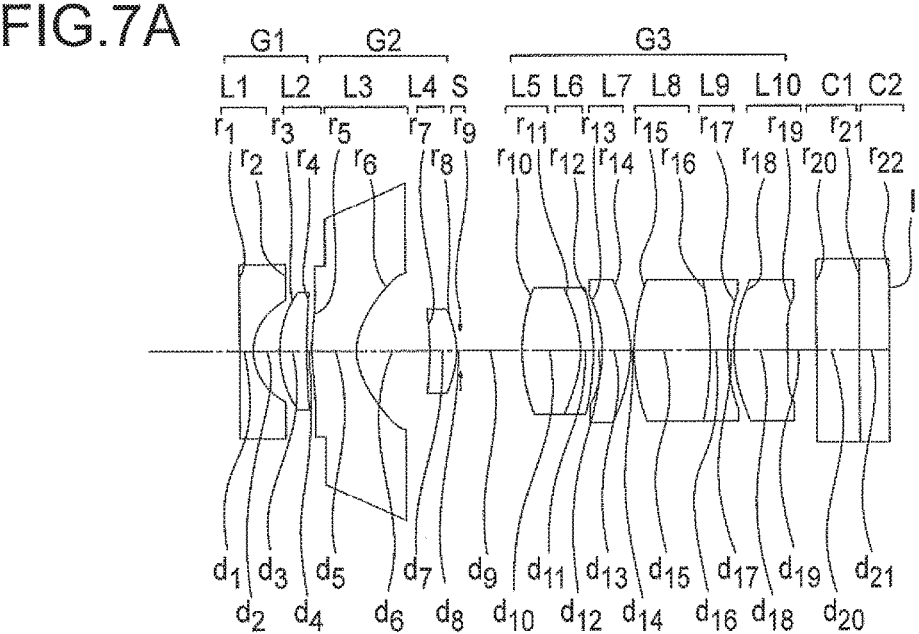
FIG. 7A and FIG. 7B are cross-sectional views showing an arrangement of a wide angle optical system according to an example 2, where.
Figure 7B:
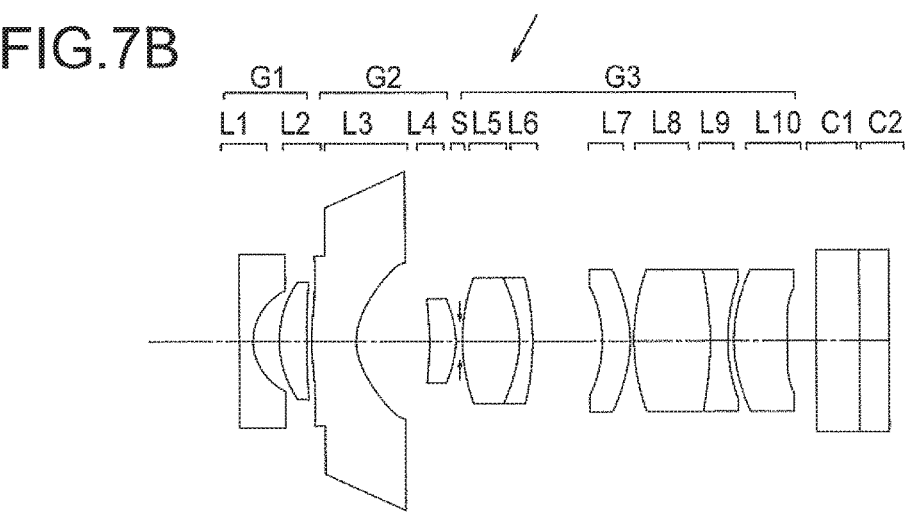

The wide angle optical system according to the example 2 will be described below. FIG. 7A and FIG. 7B are cross-sectional views showing an arrangement of the wide angle optical system according to the example 2, where, FIG. 7A is a cross-sectional view of an arrangement at a wide angle end and FIG. 7B is a cross-sectional view of an arrangement at a telephoto end.

The wide angle optical system according to the example 2 is an optical system in which the wide angle optical system according to the example 1 is let to be a variable magnification optical system. At the wide angle end, it is possible to observe both an object in front and an object on a side. Therefore, at the wide angle end, an image formation by the first optical system and an image formation by the second optical system are carried out. At the telephoto end, only the object in front can be observed. Therefore, at the telephoto end, the image formation is carried out only by the first optical system.

An optical cross-sectional view at the wide angle end of the wide angle optical system according to the example 2 is same as the optical cross-sectional view of the wide angle optical system according to the example 1. Therefore, description by using r' and d' for optical surfaces and distances in a second lens group of the second optical system is omitted. Moreover, aberration diagrams at the wide angle end of the wide angle optical system according to the example 2 are same as FIG. 5A to FIG. 5J and FIG. 6A to FIG. 6J.

Figure 8A:
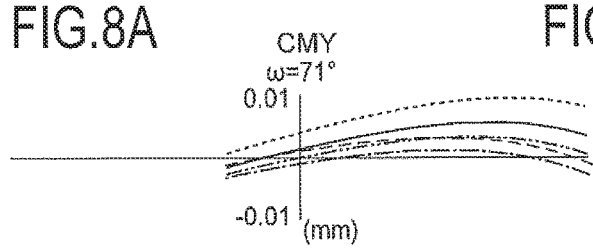
FIG. 8A, FIG. 8B, FIG. 8C, FIG. 8D, FIG. 8E, FIG. 8F, FIG. 8G, FIG. 8H, FIG. 8I, and FIG. 8J (hereinafter, 'FIG. 8A to FIG. 8J') are aberration diagrams for a first optical system, at a telephoto end of the wide angle optical system according to the example 2, where.
Figure 8B:
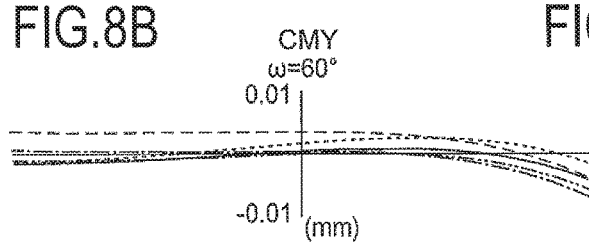
Figure 8C:
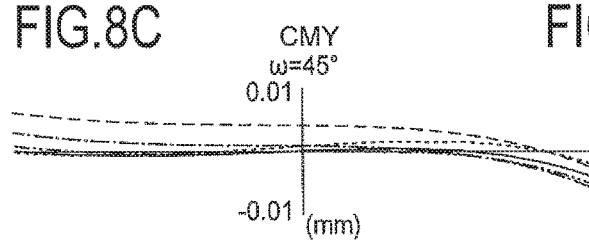
Figure 8D:
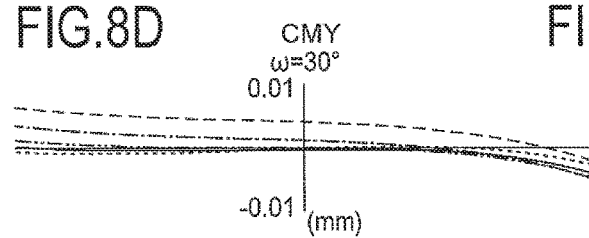
Figure 8E:
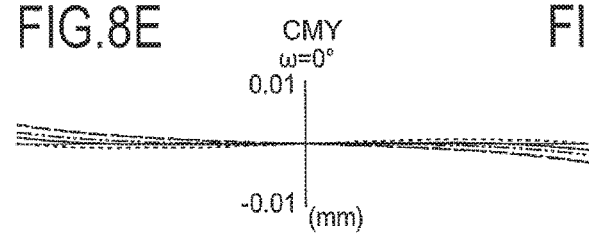
Figure 8F:
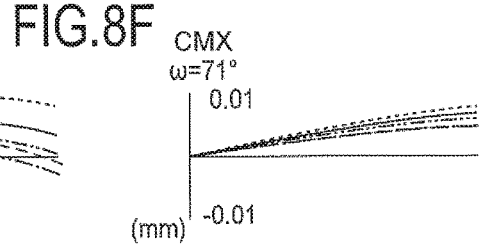
Figure 8G:
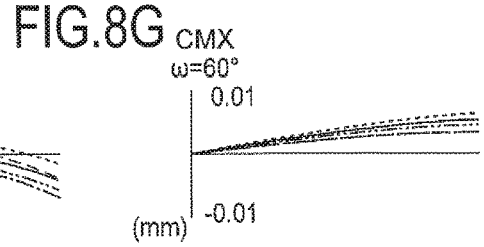
Figure 8H:
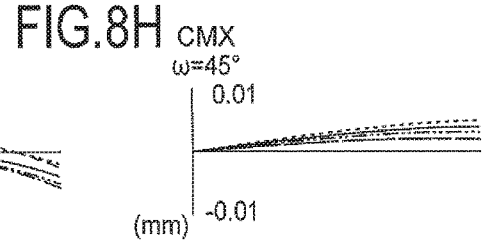
Figure 8I:
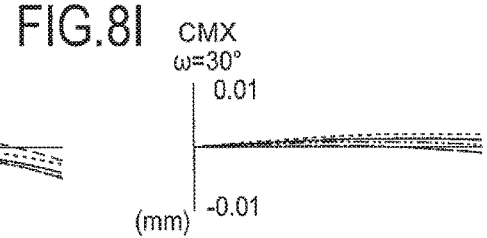
Figure 8J:
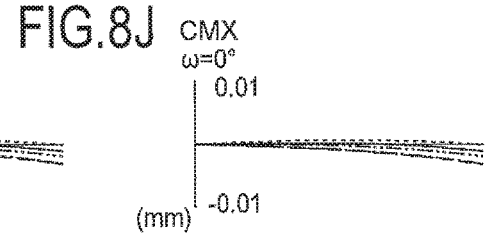

FIG. 8A to FIG. 8J are aberration diagrams for the first optical system, at the telephoto end of the wide angle optical system according to the example 2. In FIG. 8A and FIG. 8F, $\omega=71°$, in FIG. 8B and FIG. 8G, $\omega=60°$, in FIG. 8C and FIG. 8H, $\omega=45°$, in FIG. 8D and FIG. 8I, $\omega=30°$, and in FIG. 8E and FIG. 8J, $\omega=0°$.

The wide angle optical system according to the example 2, as shown in FIG. 8A and FIG. 8B, includes in order from a side of the object in front, a first lens group G1 having a negative refractive power, a second lens group G2, an aperture stop S, and a third lens group G3 having a positive refractive power. Since a specific arrangement of each lens group has been described in the example 1, the description thereof in detail is omitted here.

In the wide angle optical system according to the example 2, the third lens group G3 includes a lens that moves along an optical axis. Specifically, a cemented lens of a biconvex positive lens L5 and a negative meniscus lens L6 moves along the optical axis. Moreover, at the time of zooming from the wide angle end to the telephoto end, the cemented lens moves in a direction of moving closer to the second lens group.

Since a magnification of the wide angle optical system changes by a movement of the cemented lens, an observation field changes. Moreover, by the movement of the cemented lens, in the first optical system, a distance up to a near object becomes shorter at the telephoto end than at the wide angle end. Therefore, in the observation of the object in front, by letting it to be the telephoto end, an observation up to a location further closer to the optical system is possible.

EXAMPLE 3

Figure 9A:
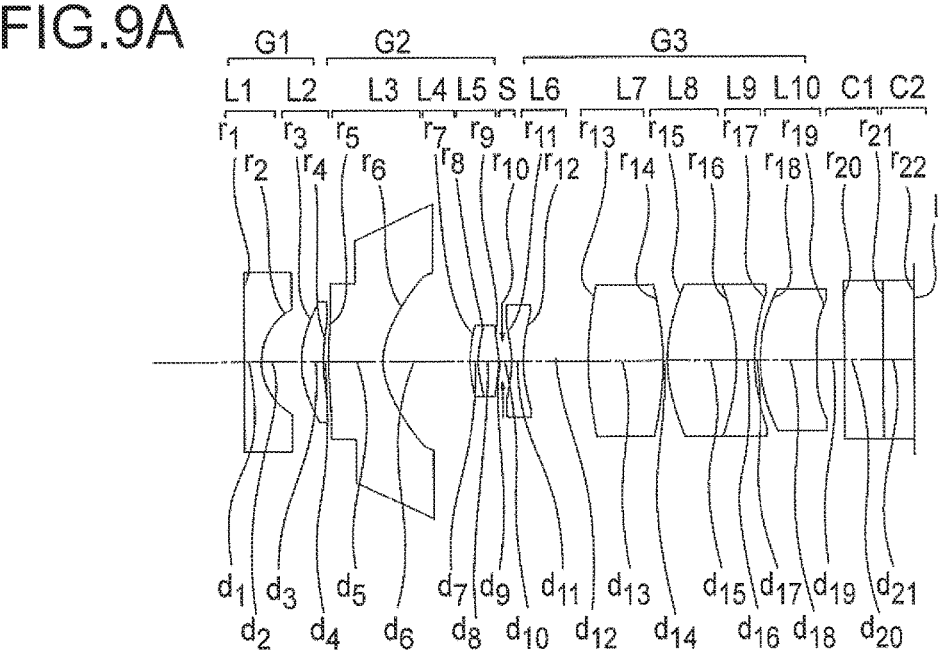
FIG. 9A and FIG. 9B are cross-sectional views showing an arrangement of a wide angle optical system according to an example 3, where.
Figure 9B:
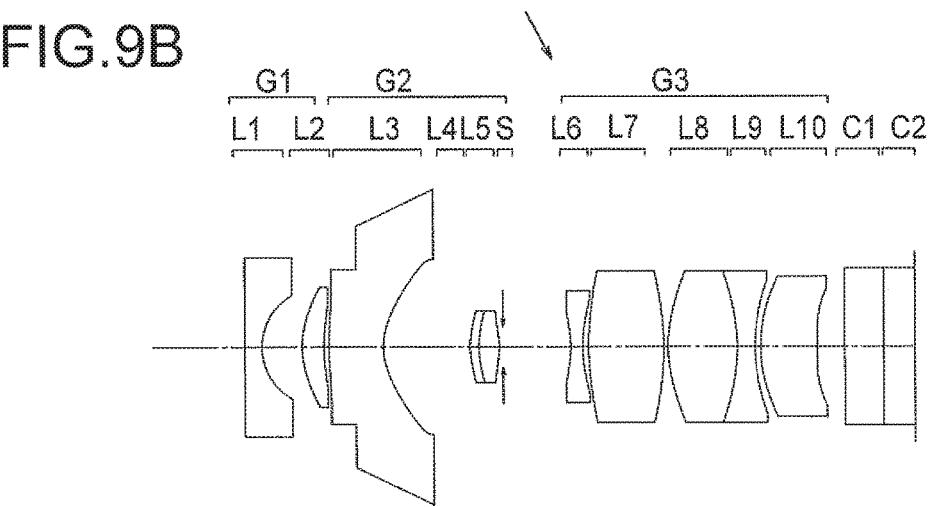

The wide angle optical system according to the example 3 will be described below. FIG. 9A and FIG. 9B are cross-sectional views showing an arrangement of the wide angle optical system according to the example 3, where, FIG. 9A is a cross-sectional view of an arrangement at a wide angle end, and FIG. 9B is a cross-sectional view of an arrangement at a telephoto end.

The wide angle optical system according to the example 3 is a wide angle optical system of a variable magnification type. At the wide angle end of the wide angle optical system according to the example 3, image formation in the second optical system is carried out. Optical surfaces and distances in a second lens group of the second optical system have been illustrated in FIG. 4B. Therefore, description by using r' and d' is omitted here.

Figure 10A:
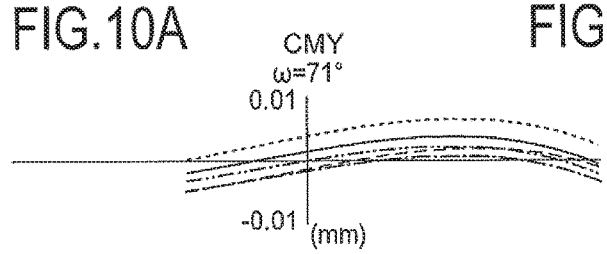
FIG. 10A, FIG. 10B, FIG. 10C, FIG. 10D, FIG. 10E, FIG. 10F, FIG. 10G, FIG. 10H, FIG. 10I, and FIG. 10J (hereinafter, 'FIG. 10A to FIG. 10J') are aberration diagrams for a first optical system, at a wide angle end of the wide angle optical system according to the example 3, where.
Figure 10F:
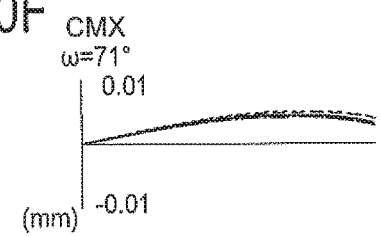
Figure 10B:
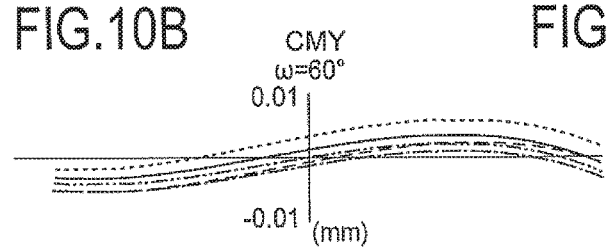
Figure 10G:
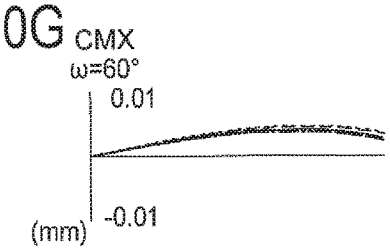
Figure 10C:
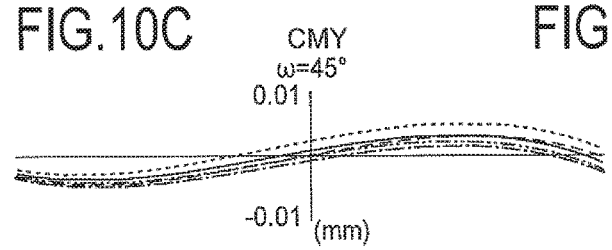
Figure 10H:
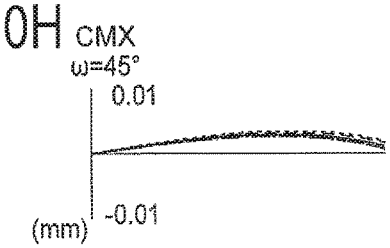
Figure 10D:
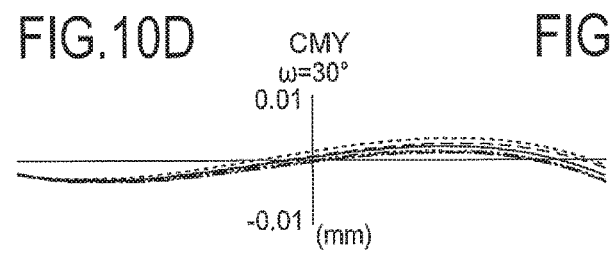
Figure 10I:
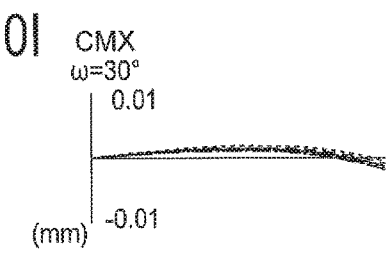
Figure 10E:
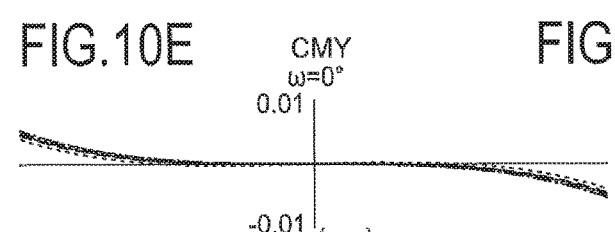
Figure 10J:
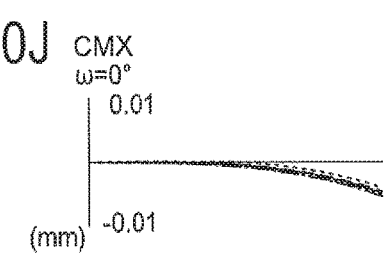

FIG. 10A to FIG. 10J are aberration diagrams for the first optical system, at the wide angle end of the wide angle optical system according to the example 3. In FIG. 10A and FIG. 10F, $\omega=71°$, in FIG. 10B and FIG. 10G, $\omega=60°$, in FIG. 10C and FIG. 10H, $\omega=45°$, in FIG. 10D and FIG. 10I, $\omega=30°$, and in FIG. 10E and FIG. 10J, $\omega=0°$.

FIG. 11A to FIG. 11J are aberration diagrams for the second optical system, at the wide angle end of the wide angle optical system according to the example 3. In FIG. 11A and FIG. 11F, $\omega'=114°$, in FIG. 11B and FIG. 11G, $\omega'=104°$, in FIG. 11C and FIG. 11H, $\omega'=94°$, in FIG. 11D and FIG. 11I, $\omega'=86°$, and in FIG. 11E and FIG. 11J, $\omega'=76°$.

FIG. 12A to FIG. 12J are aberration diagrams for the first optical system, at the telephoto end of the wide angle optical system according to the example 3. In FIG. 12A and FIG. 12F, $\omega=70°$, in FIG. 12B and FIG. 12G, $\omega=60°$, in FIG. 12C and FIG. 12H, $\omega=45°$, in FIG. 12D and FIG. 12I, $\omega=30°$, and in FIG. 12E and FIG. 12J, $\omega=0°$.

The wide angle optical system according to the example 3, as shown in FIG. 9A and FIG. 9B, includes in order from a side of an object in front, a first lens group G1 having a negative refractive power, a second lens group G2, an aperture stop S, and a third lens group G3 having a positive refractive power.

The first lens group G1 includes a planoconcave negative lens L1 of which an object side is a flat surface and a positive meniscus lens L2 having a convex surface directed toward an object side.

The second lens group G2 includes a catadioptric optical element L3, a negative meniscus lens L4 having a convex surface directed toward the object side, and a biconvex positive lens L5. Here, the negative meniscus lens L4 and the biconvex positive lens L5 are cemented.

The third lens group G3 includes a biconcave negative lens L6, a biconvex positive lens L7, a biconvex positive lens L8, a biconcave negative lens L9, and a positive meniscus lens L10 having a convex surface directed toward the object side. Here, the biconvex positive lens L8 and the biconcave negative lens L9 are cemented.

A cover glass C1 and a cover glass C2 are disposed on an image side of the third lens group G3. The cover glass C2 is a cover glass of an image pickup element. An image of an object in front and an image of an object on a side are formed on an image-side surface of the cover glass C2. Therefore, an image pickup surface of the image pickup element is positioned on the image-side surface of the cover glass C2.

An aspheric surface is provided to a total of three surfaces namely, both surfaces of the catadioptric optical element L3 and an image-side surface of the positive meniscus lens L10.

The catadioptric optical element L3 has a first surface, a second surface, and a third surface. The first surface is a surface toward the first lens group G1. The second surface is a surface toward the third lens group G3. The third surface is formed between the first surface and the second surface.

The first surface has a first transmitting surface and a first reflecting surface. The first transmitting surface is formed to include an optical axis of a first optical path. The first reflecting surface is an annular reflecting surface, and is formed around the first transmitting surface.

The second surface has a second transmitting surface and a second reflecting surface. The second transmitting surface is formed to include the optical axis of the first optical path. The second reflecting surface is an annular reflecting surface, and is formed around the second transmitting surface.

The third surface has a third transmitting surface. The third transmitting surface is a side surface of a circular truncated cone. An apex of the circular truncated cone is positioned on the side of the object in front, of the first lens group G1.

In the first optical path, the first lens group, the first transmitting surface, and the second transmitting surface are positioned in order from the side of the object in front. Since both the first surface and the second surface have a convex surface directed toward the object side, in the first optical path, the catadioptric optical element L3 functions as a negative meniscus lens.

In the second optical path, the third transmitting surface, the second reflecting surface, the first reflecting surface, and the second transmitting surface are positioned in order from the side of the object on a side. The third transmitting surface is a flat surface, the second reflecting surface is a reflecting surface which is convex toward the object side, the first reflecting surface is a reflecting surface which is convex toward the image side, and the second transmitting surface is a transmitting surface which is convex toward the object side.

The aperture stop S and the third lens group G3 are positioned in the common optical path.

In the wide angle optical system according to the example 3, the third lens group G3 includes a lens that moves along an optical axis, Specifically, the biconcave negative lens L6 moves along the optical axis. Moreover, at the time of zooming from the wide angle end to the telephoto end, the biconcave negative lens L6 moves in a direction of moving away from the second lens group G2.

Since a magnification of the wide angle optical system changes by a movement of the biconcave negative lens L6, an observation field changes. Moreover, by the movement of the biconcave negative lens L6, in the first optical system, a distance up to a near object becomes shorter at the telephoto end than at the wide angle end. Therefore, in the observation of the object in front, by letting it to be the telephoto end, an observation up to a location further closer to the optical system is possible.

Although the wide angle optical system according to the example 3 is a wide angle optical system of a variable magnification type, a position of the biconcave negative lens L6 may be fixed at a position at the wide angle end. By doing so, it is possible to let the wide angle optical system according to the example 3 to be a wide angle optical system of a single focal length type.

EXAMPLE 4

The wide angle optical system according to the example 4 will be described below. FIG. 13A and FIG. 13B are cross-sectional views showing an arrangement of the wide angle optical system according to the example 4, where, FIG. 13A is a cross-sectional view of an arrangement at a wide angle end, and FIG. 13B is a cross-sectional view of an arrangement at a telephoto end.

The wide angle optical system according to the example 4 is a variable magnification optical system. At the wide angle end of the wide angle optical system according to the example 4, image formation in a second optical system is also carried out. Optical surfaces and distances in a second lens group of the second optical system have been illustrated in FIG. 4B. Therefore, description by using r' and d' is omitted here.

Figure 14A:
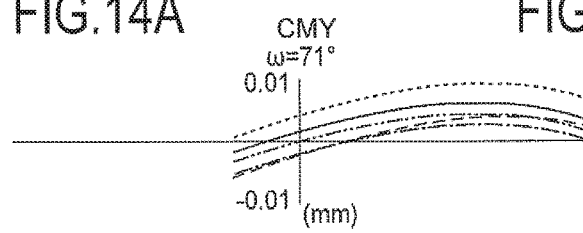
FIG. 14A, FIG. 14B, FIG. 14C, FIG. 14D, FIG. 14E, FIG. 14F, FIG. 14G, FIG. 14H, FIG. 14I, and FIG. 14J (hereinafter, 'FIG. 14A to FIG. 14J') are aberration diagrams for a first optical system, at a wide angle end of the wide angle optical system according to the example 4, where.
Figure 14F:
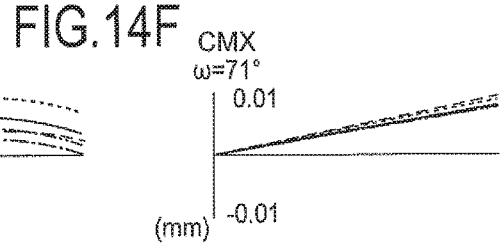
Figure 14B:
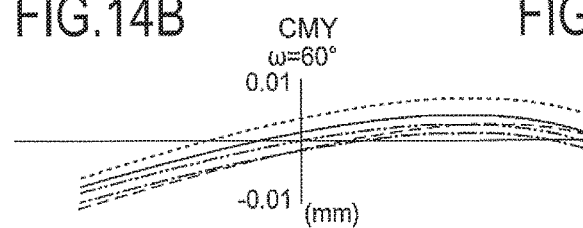
Figure 14G:
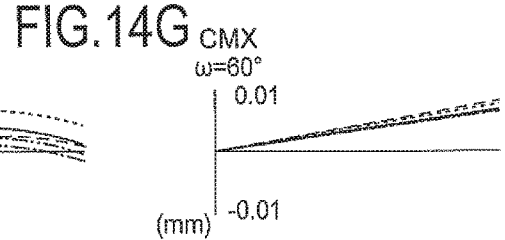
Figure 14C:
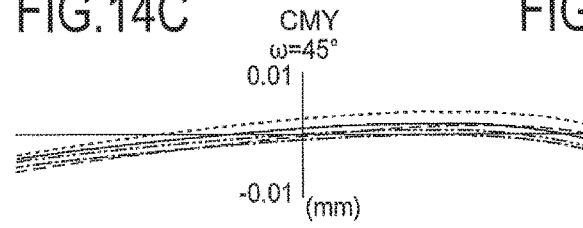
Figure 14H:
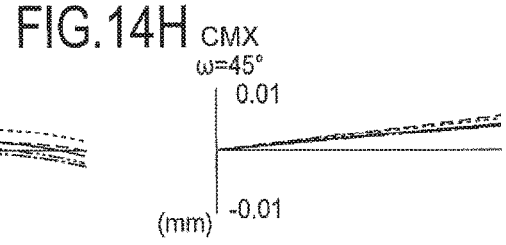
Figure 14D:
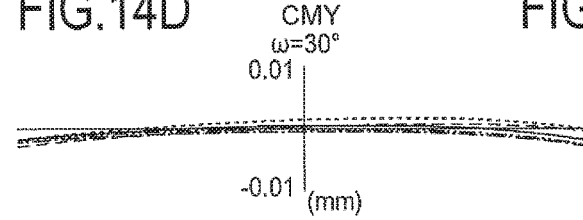
Figure 14I:
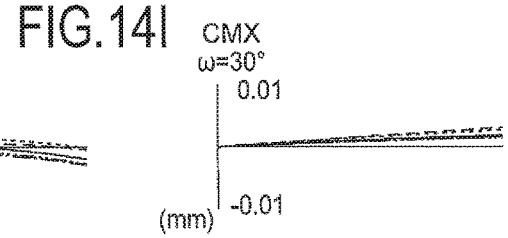
Figure 14E:
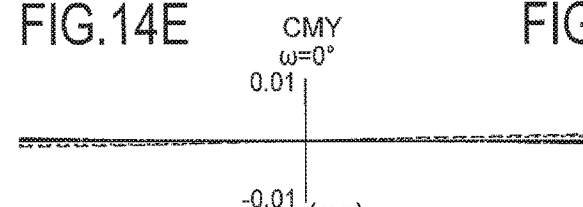
Figure 14J:
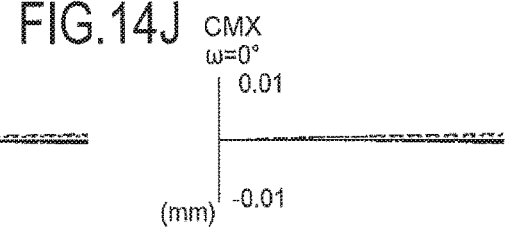

FIG. 14A to FIG. 14J are aberration diagrams for the first optical system, at the wide angle end of the wide angle optical system according to the example 4. In FIG. 14A and FIG. 14F, ω=71°, in FIG. 14B and FIG. 14G, ω=60°, in FIG. 14C and FIG. 14H, ω=45°, in FIG. 14D and FIG. 14I, ω=30°, and in FIG. 14E and FIG. 14J, ω=0°.

Figure 15A:
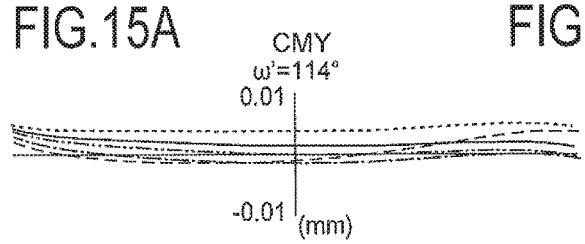
Figure 15F:
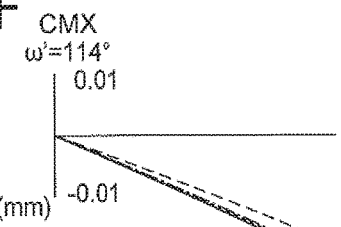

FIG. 15A to FIG. 15J are aberration diagrams for the second optical system, at the wide angle end of the wide angle optical system according to the example 4. In FIG. 15A and FIG. 15F, ω'=114°, in FIG. 15B and FIG. 15G, ω'=104°, in FIG. 15C and FIG. 15H, ω'=94°, in FIG. 15D and FIG. 15I, ω'=86°, and in FIG. 15E and FIG. 15J, θ'=76°.

Figure 16A:
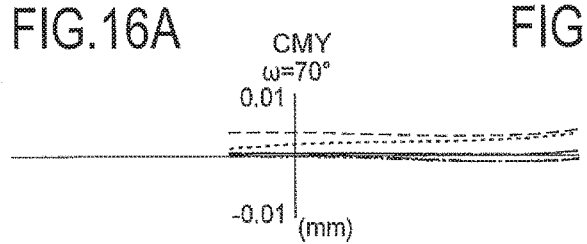
FIG. 16A, FIG. 16B, FIG. 16C, FIG. 16D, FIG. 16E, FIG. 16F, FIG. 16G, FIG. 16H, FIG. 16I, and FIG. 16J (hereinafter, 'FIG. 16A to FIG. 16J) are aberration diagrams for the first optical system, at a telephoto end of the wide angle optical system according to the example 4, where.
Figure 16F:
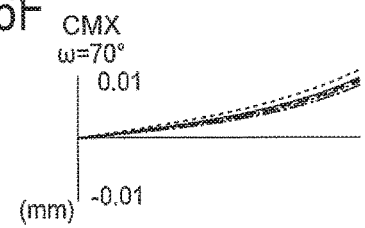
Figure 16B:
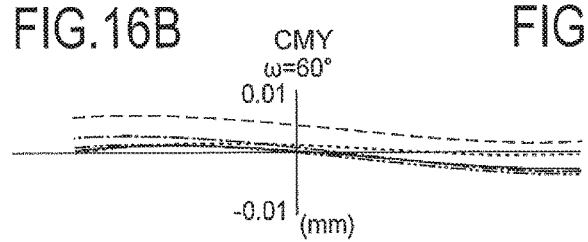
Figure 16G:
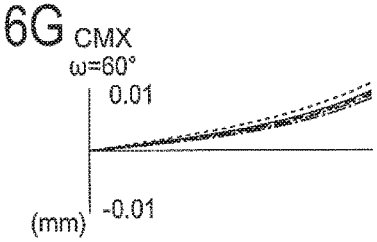
Figure 16C:
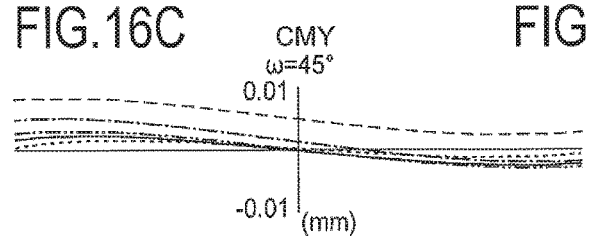
Figure 16H:
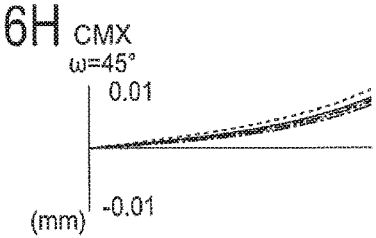
Figure 16D:
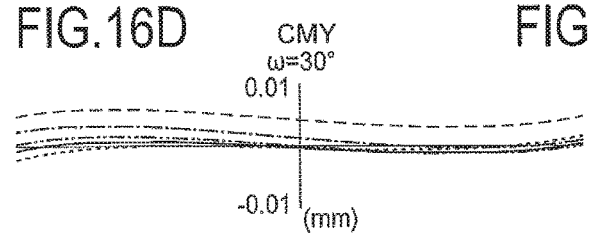
Figure 16I:
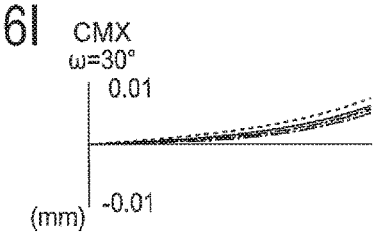
Figure 16E:
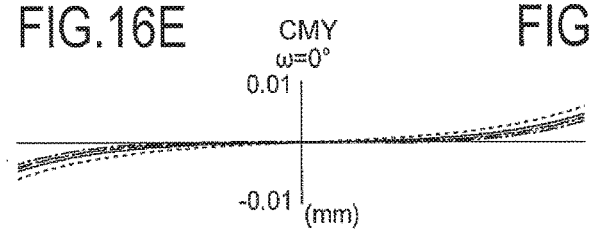
Figure 16J:
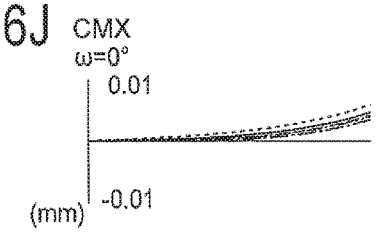

FIG. 16A to FIG. 16J are aberration diagrams for the first optical system, at the telephoto end of the wide angle optical system according to the example 4. In FIG. 16A and FIG. 16F, ω=70°, in FIG. 16B and FIG. 16G, ω=60°, in FIG. 16C and FIG. 16H, ω=45°, in FIG. 16D and FIG. 16I, ω=30°, and in FIG. 16E and FIG. 16J, ω=0°.

The wide angle optical system according to the example 4, as shown in FIG. 13A and FIG. 13B, includes in order from a side of an object in front, a first lens group G1 having a negative refractive power, a second lens group G2, an aperture stop S, and a third lens group G3 having a positive refractive power.

The first lens group G1 includes a planoconcave negative lens L1 of which an object side is a flat surface and a positive meniscus lens L2 having a convex surface directed toward an object side.

The second lens group G2 includes a catadioptric optical element L3, a negative meniscus lens L4 having a convex surface directed toward the object side, and a biconvex positive lens L5. Here, the negative meniscus lens L4 and the biconvex positive lens L5 are cemented.

The third lens group G3 includes a negative meniscus lens L6 having a convex surface directed toward an image side, a biconvex positive lens L7, a biconvex positive lens L8, a biconcave negative lens L9, and a positive meniscus lens L10 having a convex surface directed toward the object side. Here, the biconvex positive lens L8 and the biconcave negative lens L9 are cemented.

A cover glass C1 and a cover glass C2 are disposed on an image side of the third lens group G3. The cover glass C2 is a cover glass of an image pickup element. An image of an object in front and an image of an object on a side are formed on an image-side surface of the cover glass C2. Therefore, an image pickup surface of the image pickup element is positioned on the image-side surface of the cover glass C2.

An aspheric surface is provided to a total of three surfaces namely, both surfaces of the catadioptric optical element L3 and an image-side surface of the positive meniscus lens L10.

The catadioptric optical element L3 has a first surface, a second surface, and a third surface. The first surface is a surface toward the first lens group G1. The second surface is a surface toward the third lens group G3. The third surface is formed between the first surface and the second surface.

The first surface has a first transmitting surface and a first reflecting surface. The first transmitting surface is formed to include an optical axis of a first optical path. The first reflecting surface is an annular reflecting surface, and is formed around the first transmitting surface.

The second surface has a second transmitting surface and a second reflecting surface. The second transmitting surface is formed to include the optical axis of the first optical path.

The second reflecting surface is an annular reflecting surface, and is formed around the second transmitting surface.

The third surface has a third transmitting surface. The third transmitting surface is a side surface of a circular truncated cone. An apex of the circular truncated cone is positioned on the side of the object in front, of the first lens group G1.

In the first optical path, the first lens group, the first transmitting surface, and the second transmitting surface are positioned in order from the side of the object in front. Since both the first surface and the second surface have a convex surface directed toward the object side, in the first optical path, the catadioptric optical element L3 functions as a negative meniscus lens.

In the second optical path, the third transmitting surface, the second reflecting surface, the first reflecting surface, and the second transmitting surface are positioned in order from the side of the object on a side. The third transmitting surface is a flat surface, the second reflecting surface is a reflecting surface which is convex toward the object side, the first reflecting surface is a reflecting surface which is convex toward the image side, and the second transmitting surface is a transmitting surface which is convex toward the object side.

The aperture stop S and the third lens group G3 are positioned in the common optical path.

In the wide angle optical system according to the example 4, the third lens group includes a lens that moves along an optical axis. Specifically, the biconvex positive lens L7 moves along the optical axis. Moreover, at the time of zooming from the wide angle end to the telephoto end, the biconvex positive lens L7 moves in a direction of moving closer to the second lens group G2.

Since a magnification of the wide angle optical system changes by a movement of the biconvex positive lens L7, an observation field changes. Moreover, by the movement of the biconvex positive lens L7, in the first optical system, a distance up to a near object becomes shorter at the telephoto end than at the wide angle end. Therefore, in the observation of the object in front, by letting it to be the telephoto end, an observation up to a location further closer to the optical system is possible.

Although the wide angle optical system according to the example 4 is a wide angle optical system of a variable magnification type, a position of the biconvex positive lens L7 may be fixed at a position at the wide angle end. By doing so, it is possible to let the wide angle optical system according to the example 4 to be a wide angle optical system of a single focal length type.

Numerical data of each example described above is shown below. In Surface data, r and r' denote radius of curvature of each lens surface, d and d' denote a distance between respective lens surfaces, nd denotes a refractive index of each lens for d-line, vd denotes an Abbe number for each optical element. In Various data, f denotes a focal length of the overall first optical system, ω denotes a maximum angle of view in the first optical system, ω' denotes a maximum angle of view in the second optical system, FNO. denotes an F number, IH denotes a maximum image height in the first optical system, IH' denotes a maximum image height in the second optical system, OD denotes an object distance, Δ denotes a distance from an object side surface of the catadioptric optical element to an apex of the circular truncated cone, α denotes an apex angle of the circular truncated cone, WE denotes a wide angle end, and TE denotes a telephoto end. Moreover, each unit of r, r', d, d', f, IH, IH', OD, and Δ is mm, and each unit of ω, ω', and α is °. Moreover, in the second optical system, an object on a side is positioned in a direction substantially orthogonal to the optical axis.

A shape of an aspheric surface is defined by the following expression where the direction of the optical axis is represented by z, the direction orthogonal to the optical axis is represented by y, a conical coefficient is represented by K, aspheric surface coefficients are represented by A4, A6, A8, A10:

$$Z=(y^2/r)/[1+\{1-(1+k)(y/r)^2\}^{1/2}]+A4y^4+A6y^6+A8y^8+A10y^{10}$$

Further, in the aspherical surface coefficients, 'E-n' (where, n is an integral number) indicates '$10^{-n}$'. Moreover, these symbols are commonly used in the following numerical data for each example.

EXAMPLE 1

| Unit mm First optical system | | | | |
|---|---|---|---|---|
| Surface data | | | | |
| Surface no. | r | d | nd | vd |
| Object plane | ∞ | 8.485108 | | |
| 1 | ∞ | 0.350000 | 1.88300 | 40.8 |
| 2 | 1.32147 | 0.555744 | | |
| 3 | 2.40000 | 0.600000 | 1.92286 | 18.9 |
| 4 | 10.81652 | 0.100000 | | |
| 5* | 5.04004 | 1.000000 | 1.88300 | 40.8 |
| 6* | 1.09155 | 1.639740 | | |
| 7 | −4.87017 | 0.600000 | 1.51633 | 64.1 |
| 8 | −2.15000 | 0.100000 | | |
| 9(Stop) | ∞ | 1.387151 | | |
| 10 | 4.06571 | 1.250000 | 1.72916 | 54.7 |
| 11 | −2.91110 | 0.300000 | 1.80518 | 25.4 |
| 12 | −6.00710 | 0.207033 | | |
| 13 | −2.82701 | 0.600000 | 1.78800 | 47.4 |
| 14 | −3.35000 | 0.100000 | | |
| 15 | 4.67925 | 1.700000 | 1.72916 | 54.7 |
| 16 | −8.09875 | 0.400000 | 1.84666 | 23.8 |
| 17 | 4.66502 | 0.100000 | | |
| 18 | 3.45000 | 1.200000 | 1.51633 | 64.1 |
| 19* | 388.82555 | 0.662065 | | |
| 20 | ∞ | 0.900000 | 1.51633 | 64.1 |
| 21 | ∞ | 0.700000 | 1.51633 | 64.1 |
| 22(Image plane) | ∞ | 0.000000 | | |

| Aspherical surface data |
|---|
| 5th surface |
| K = 0 A4 = −0.594274E−01, A6 = 0.314951E−01, A8 = −0.806989E−02, A10 = 0 |
| 6th surface |
| K = −0.617507 A4 = −0.139675E+00, A6 = −0.502184E−02, A8 = 0.186987E−01, A10 = −0.582054E−02 |
| 19th surface |
| K = 0 A4 = 0.159249E−01, A6 = 0.727058E−01, A8 = −0.600000E−01, A10 = 0.245353E−01 |

| Various data | |
|---|---|
| f | 0.845 |
| ω | 71 |
| FNO. | 3.7 |
| IH | 0.79 |

Second Optical System

The second surface and the third surface are reflecting surfaces. For surfaces on an image side of the sixth surface in the second optical system, since numerical values of the ninth surface to the 22$^{nd}$ surface of the first optical system have been listed, surface numbers are not successive.

Surface data

| Surface no. | r' | d' | nd | vd |
|---|---|---|---|---|
| Object plane | ∞ | 20.000000 | | |
| 1 | Conical surface | 0.000000 | 1.88300 | 40.8 |
| 2* | 1.09155 | −1.000000 | 1.88300 | 40.8 |
| 3* | 5.04004 | 1.000000 | 1.88300 | 40.8 |
| 4* | 1.09155 | 1.639740 | | |
| 5 | −4.87017 | 0.600000 | 1.51633 | 64.1 |
| 6 | −2.15000 | 0.100000 | | |

| (Surface no.) | r | d | nd | vd) |
|---|---|---|---|---|
| 9(Stop) | ∞ | 1.387151 | | |
| 10 | 4.06571 | 1.250000 | 1.72916 | 54.7 |
| 11 | −2.91110 | 0.300000 | 1.80518 | 25.4 |
| 12 | −6.00710 | 0.207033 | | |
| 13 | −2.82701 | 0.600000 | 1.78800 | 47.4 |
| 14 | −3.35000 | 0.100000 | | |
| 15 | 4.67925 | 1.700000 | 1.72916 | 54.7 |
| 16 | −8.09875 | 0.400000 | 1.84666 | 23.8 |
| 17 | 4.66502 | 0.100000 | | |
| 18 | 3.45000 | 1.200000 | 1.51633 | 64.1 |
| 19* | 388.82555 | 0.662065 | | |
| 20 | ∞ | 0.900000 | 1.51633 | 64.1 |
| 21 | ∞ | 0.700000 | 1.51633 | 64.1 |
| 22(Image plane) | ∞ | 0.000000 | | |

Aspherical surface data

2nd surface

K = −0.617507
A4 = −0.139675E+00, A6 = −0.502184E−02,
A8 = 0.186987E−01, A10 = −0.582054E−02
3rd surface K = 0
A4 = −0.594274E−01, A6 = 0.314951E−01,
A8 = −0.806989E−02, A10 = 0
4th surface K = −0.617507
A4 = −0.139675E+00, A6 = −0.502184E−02,
A8 = 0.186987E−01, A10 = −0.582054E−02
19th surface K = 0
A4 = 0.159249E−01, A6 = 0.727058E−01,
A8 = −0.600000E−01, A10 = 0.245353E−01

Various data

| | |
|---|---|
| ω' | 73 to 116 |
| IH' | 1.19 |
| Δ | 5.6 |
| α | 49 |

EXAMPLE 2

Unit mm
First optical system

Surface data

| Surface no. | r | d | nd | vd |
|---|---|---|---|---|
| Object plane | ∞ | (Variable) | | |
| 1 | ∞ | 0.350000 | 1.88300 | 40.8 |
| 2 | 1.32147 | 0.555744 | | |
| 3 | 2.40000 | 0.600000 | 1.92286 | 18.9 |
| 4 | 10.81652 | 0.100000 | | |
| 5* | 5.04004 | 1.000000 | 1.88300 | 40.8 |
| 6* | 1.09155 | 1.639740 | | |
| 7 | −4.87017 | 0.600000 | 1.51633 | 64.1 |
| 8 | −2.15000 | 0.100000 | | |
| 9(Stop) | ∞ | (Variable) | | |
| 10 | 4.06571 | 1.250000 | 1.72916 | 54.7 |
| 11 | −2.91110 | 0.300000 | 1.80518 | 25.4 |
| 12 | −6.00710 | (Variable) | | |
| 13 | −2.82701 | 0.600000 | 1.78800 | 47.4 |
| 14 | −3.35000 | 0.100000 | | |
| 15 | 4.67925 | 1.700000 | 1.72916 | 54.7 |
| 16 | −8.09875 | 0.400000 | 1.84666 | 23.8 |
| 17 | 4.66502 | 0.100000 | | |
| 18 | 3.45000 | 1.200000 | 1.51633 | 64.1 |
| 19* | 388.82555 | 0.662065 | | |
| 20 | ∞ | 0.900000 | 1.51633 | 64.1 |
| 21 | ∞ | 0.700000 | 1.51633 | 64.1 |
| 22(Image plane) | ∞ | 0.000000 | | |

Aspherical surface data

5th surface

K = 0
A4 = −0.594274E−01, A6 = 0.314951E−01,
A8 = −0.806989E−02, A10 = 0
6th surface K = −0.617507
A4 = −0.139675E+00, A6 = −0.502184E−02,
A8 = 0.186987E−01, A10 = −0.582054E−02
19th surface K = 0
A4 = 0.159249E−01, A6 = 0.727058E−01,
A8 = −0.600000E−01, A10 = 0.245353E−01

Various data

| | WE | TE |
|---|---|---|
| f | 0.845 | 1.161 |
| ω | 71 | 71 |
| FNO. | 3.7 | 3.7 |
| IH | 0.79 | 0.79 |
| OD | 8.485108 | 4.094054 |
| d9 | 1.387151 | 0.100000 |
| d12 | 0.207033 | 1.494234 |

Second Optical System

Since the second optical system in example 2 is same the second optical system in example 2, description of Numerical data is omitted.

EXAMPLE 3

Unit mm
First optical system

Surface data

| Surface no. | r | d | nd | vd |
|---|---|---|---|---|
| Object plane | ∞ | (Variable) | | |
| 1 | ∞ | 0.350000 | 1.88300 | 40.8 |
| 2 | 1.47964 | 0.890904 | | |
| 3 | 2.40000 | 0.472230 | 1.95906 | 17.5 |
| 4 | 4.71951 | 0.100000 | | |
| 5* | 10.46702 | 1.249237 | 1.88300 | 40.8 |
| 6* | 1.59921 | 2.000000 | | |
| 7 | 3.61069 | 0.150000 | 1.84666 | 23.8 |
| 8 | 2.17434 | 0.450000 | 1.72916 | 54.7 |
| 9 | −3.05447 | 0.100000 | | |
| 10(Stop) | ∞ | (Variable) | | |
| 11 | −3.25205 | 0.250000 | 1.49700 | 81.6 |
| 12 | 3.67111 | (Variable) | | |
| 13 | 6.64263 | 1.700000 | 1.72916 | 54.7 |
| 14 | −6.10176 | 0.100000 | | |
| 15 | 3.60000 | 1.550000 | 1.72916 | 54.7 |
| 16 | −4.76451 | 0.400000 | 1.84666 | 23.8 |
| 17 | 4.50000 | 0.100000 | | |
| 18 | 3.32064 | 1.300000 | 1.51633 | 64.1 |
| 19* | 14.04961 | 0.600000 | | |
| 20 | ∞ | 0.900000 | 1.51633 | 64.1 |
| 21 | ∞ | 0.700000 | 1.51633 | 64.1 |
| 22(Image plane) | ∞ | 0.000000 | | |

Aspherical surface data

5th surface

K = 0
A4 = −0.162812E−01, A6 = 0.863083E−02,
A8 = −0.217514E−02, A10 = 0

6th surface

K = −0.373424
A4 = −0.475711E−02, A6 = −0.395806E−01,
A8 = 0.150952E−01, A10 = −0.224984E−02

19th surface

K = 0
A4 = 0.353194E−01, A6 = −0.182054E−02,
A8 = 0.520470E−05, A10 = 0.149364E−02

Various data

| | WE | TE |
|---|---|---|
| f | 0.849 | 1.217 |
| ω | 69 | 69 |
| FNO. | 41 | 4.1 |
| IH | 0.79 | 0.79 |
| OD | 8.484053 | 4.554102 |
| d10 | 0.200000 | 1.537898 |
| d12 | 1.437629 | 0.100000 |

Second Optical System

The second surface and the third surface are reflecting surfaces. For surfaces on an image side of the seventh surface in the second optical system, since numerical values of the tenth surface to the 22$^{nd}$ surface of the first optical system have been listed, surface numbers are not successive.

Surface data

| Surface no. | r' | d' | nd | vd |
|---|---|---|---|---|
| Object plane | ∞ | 20.000000 | | |
| 1 | Conical surface | 0.000000 | 1.88300 | 40.8 |
| 2* | 1.59921 | −1.249237 | 1.88300 | 40.8 |
| 3* | 10.46702 | 1.249237 | 1.88300 | 40.8 |
| 4* | 1.59921 | 2.000000 | | |
| 5 | 3.61069 | 0.150000 | 1.84666 | 23.8 |
| 6 | 2.17434 | 0.450000 | 1.72916 | 54.7 |
| 7 | −3.05447 | 0.100000 | | |
| (Surface no.) | r | d | nd | vd |
| 10(Stop) | ∞ | 0.200000 | | |
| 11 | −3.25205 | 0.250000 | 1.49700 | 81.6 |
| 12 | 3.67111 | 1.437629 | | |
| 13 | 6.64263 | 1.700000 | 1.72916 | 54.7 |
| 14 | −6.10176 | 0.100000 | | |
| 15 | 3.60000 | 1.550000 | 1.72916 | 54.7 |
| 16 | −4.76451 | 0.400000 | 1.84666 | 23.8 |
| 17 | 4.50000 | 0.100000 | | |
| 18 | 3.32064 | 1.300000 | 1.51633 | 64.1 |
| 19* | 14.04961 | 0.600000 | | |
| 20 | ∞ | 0.900000 | 1.51633 | 64.1 |
| 21 | ∞ | 0.700000 | 1.51633 | 64.1 |
| 22(Image plane) | ∞ | 0.000000 | | |

Aspherical surface data

2nd surface

K = −0.373424
A4 = −0.475711E−02, A6 = −0.395806E−01,
A8 = 0.150952E−01, A10 = −0.224984E−02

3rd surface

K = 0
A4 = −0.162812E−01, A6 = 0.863083E−02,
A8 = −0.217514E−02, A10 = 0

4th surface

K = −0.373424
A4 = −0.475711E−02, A6 = −0.395806E−01,
A8 = 0.150952E−01, A10 = −0.224984E−02

19th surface

K = 0
A4 = 0.353194E−01, A6 = −0.182054E−02,
A8 = 0.520470E−05, A10 = 0.149364E−02

Various data

| | |
|---|---|
| ω' | 73 to 116 |
| IH' | 1.19 |
| Δ | 56 |
| α | 49 |

EXAMPLE 4

Unit mm
First optical system

Surface data

| Surface no. | r | d | nd | vd |
|---|---|---|---|---|
| Object plane | ∞ | (Variable) | | |
| 1 | ∞ | 0.350000 | 1.88300 | 40.8 |
| 2 | 1.43828 | 0.542918 | | |
| 3 | 2.40000 | 0.450000 | 1.95906 | 17.5 |
| 4 | 5.26841 | 0.136054 | | |
| 5* | 11.46595 | 1.000000 | 1.88300 | 40.8 |
| 6* | 1.56049 | 1.886471 | | |
| 7 | 8.01652 | 1.542793 | 1.84666 | 23.8 |
| 8 | 3.19918 | 0.800000 | 1.72916 | 54.7 |
| 9 | −2.06761 | 0.100000 | | |
| 10(Stop) | ∞ | 0.200000 | | |
| 11 | −1.60720 | 0.250000 | 1.49700 | 81.6 |
| 12 | −60.79891 | (Variable) | | |

-continued

Unit mm
First optical system

| | | | | |
|---|---|---|---|---|
| 13 | 8.95080 | 1.076000 | 1.72916 | 54.7 |
| 14 | −4.61592 | (Variable) | | |
| 15 | 3.82815 | 1.550000 | 1.72916 | 54.7 |
| 16 | −4.61919 | 0.400000 | 1.84666 | 23.8 |
| 17 | 5.73702 | 0.160076 | | |
| 18 | 9.70034 | 1.300000 | 1.51633 | 64.1 |
| 19* | 12.05176 | 0.665059 | | |
| 20 | ∞ | 0.900000 | 1.51633 | 64.1 |
| 21 | ∞ | 0.700000 | 1.51633 | 64.1 |
| 22(Image plane) | ∞ | 0.000000 | | |

Aspherical surface data

5th surface

K = 0
A4 = −0.848532E−04, A6 = 0.582300E−03,
A8 = −0.504512E−03, A10 = 0

6th surface

K = −0.326206
A4 = −0.239027E−01, A6 = −0.281927E−01,
A8 = 0.141001E−01, A10 = −0.278028E−02

19th surface

K = 0
A4 = 0.273885E−01, A6 = 0.311887E−01,
A8 = −0.297459E−01, A10 = 0.128331E−01

Various data

| | WE | TE |
|---|---|---|
| f | 0.796 | 1.123 |
| ω | 71 | 71 |
| FNO. | 3.7 | 3.7 |
| IH | 0.79 | 0.79 |
| OD | 8.495342 | 4.513655 |
| d12 | 1.806782 | 0.164996 |
| d14 | 0.183855 | 1.825654 |

Second Optical System

The second surface and the third surface are reflecting surfaces. For surfaces on an image side of the seventh surface in the second optical system, since numerical values of the tenth surface to the $22^{nd}$ surface of the first optical system have been listed, surface numbers are not successive.

Surface data

| Surface no. | r' | d' | nd | vd |
|---|---|---|---|---|
| Object plane | ∞ | 20.000000 | | |
| 1 | Conical surface | 0.000000 | 1.88300 | 40.8 |
| 2* | 1.56049 | −1.000000 | 1.88300 | 40.8 |
| 3* | 11.46595 | 1.000000 | 1.88300 | 40.8 |
| 4* | 1.56049 | 1.886471 | | |
| 5 | 8.01652 | 1.542793 | 1.84666 | 23.8 |
| 6 | 3.19918 | 0.800000 | 1.72916 | 54.7 |
| 7 | −2.06761 | 0.100000 | | |

| (Surface no. | r | d | nd | vd) |
|---|---|---|---|---|
| 10(Stop) | ∞ | 0.200000 | | |
| 11 | −1.60720 | 0.250000 | 1.49700 | 81.6 |
| 12 | −60.79891 | 1.806782 | | |
| 13 | 8.95080 | 1.076000 | 1.72916 | 54.7 |
| 14 | −4.61592 | 0.183855 | | |
| 15 | 3.82815 | 1.550000 | 1.72916 | 54.7 |
| 16 | −4.61919 | 0.400000 | 1.84666 | 23.8 |
| 17 | 5.73702 | 0.160076 | | |
| 18 | 9.70034 | 1.300000 | 1.51633 | 64.1 |
| 19* | 12.05176 | 0.665059 | | |
| 20 | ∞ | 0.900000 | 1.51633 | 64.1 |
| 21 | ∞ | 0.700000 | 1.51633 | 64.1 |
| 22(Image plane) | ∞ | 0.000000 | | |

Aspherical surface data

2nd surface

K = −0.326206
A4 = −0.239027E−01, A6 = −0.281927E−01,
A8 = 0.141001E−01, A10 = −0.278028E−02

3rd surface

K = 0.000000
A4 = −0.848532E−04, A6 = 0.582300E−03,
A8 = −0.504512E−03, A10 = 0

4th surface

K = −0.326206
A4 = −0.239027E−01, A6 = −0.281927E−01,
A8 = 0.141001E−01, A10 = −0.278028E−02

19th surface

K = 0
A4 = 0.273885E−01, A6 = 0.311887E−01,
A8 = −0.297459E−01, A10 = 0.128331E−01

Various data

| | |
|---|---|
| ω' | 72 to 116 |
| IH' | 1.2 |
| Δ | 5.6 |
| α | 49 |

Next, values of conditional expressions (1) to (7) in each example are given below. '-' (hyphen) indicates that there is no corresponding arrangement.

| Conditional Expression | Example1 | Example2 |
|---|---|---|
| (1)νp | 189 | 189 |
| νn | 40.8 | 40.8 |
| (2)\|φp\| | 0.313 | 0.313 |
| \|φn\| | 0.672 | 0.672 |
| (3)θk | 73 | 73 |
| α | 49 | 49 |
| (4)(\|φn\|/νn)/(φp/νp) | 0.994 | 0.994 |
| (5)νn | 40.8 | 40.8 |
| (6)νp | 18.9 | 18.9 |
| (7)\|f3/fi\| | — | 0.825 |

| Conditional Expression | Example3 | Example4 |
|---|---|---|
| (1)νp | 17.5 | 17.5 |
| νn | 40.8 | 40.8 |
| (2)\|φp\| | 0.219 | 0.238 |
| \|φn\| | 0.600 | 0.618 |
| (3)θk | 73 | 72 |
| α | 49 | 49 |
| (4)(\|φn\|/νn)/(φp/νp) | 1.175 | 1.114 |
| (5)νn | 40.8 | 40.8 |
| (6)νp | 17.5 | 17.5 |
| (7)\|f3/fi\| | 1.084 | 1.026 |

The wide angle optical system according to the present invention includes the following wide angle optical systems.

(Appended Mode 1)

A wide angle optical system having a first optical path along which light from an object in front passes, a second optical path along which light from an object on a side passes, and a common optical path along which the light from the object in front and the light from the object on a side pass, comprising in order from a side of the object in front:

a first lens group having a negative refractive power;
a second lens group having a catadioptric optical element;
an aperture stop; and
a third lens group having a positive refractive power, wherein
the first lens group includes a positive lens and a negative lens, and
the catadioptric optical element has a first surface, a second surface, and a third surface that is formed between the first surface and the second surface, and
the first surface has a first transmitting surface and a first reflecting surface, and
the first transmitting surface is formed to include an optical axis of the first optical path, and
the first reflecting surface is an annular reflecting surface, and is formed around the first transmitting surface, and
the second surface has a second transmitting surface and a second reflecting surface, and
the second transmitting surface is formed to include the optical axis of the first optical path, and
the second reflecting surface is an annular reflecting surface, and is formed around the second transmitting surface, and
the third surface has a third transmitting surface, and
the third transmitting surface is a side surface of a circular truncated cone, and
an apex of the circular truncated cone is positioned on the side of the object in front of the first lens group, and
in the first optical path, the first lens group, the first transmitting surface, and the second transmitting surface are positioned in order from the side of the object in front, and
in the second optical path, the third transmitting surface, the second reflecting surface, the first reflecting surface, and the second transmitting surface are positioned in order from the side of the object on a side, and
the aperture stop and the third lens group are positioned in the common optical path, and
a direction of a chromatic aberration of magnification which occurs in the catadioptric optical element is same for all light beams that are incident on the third transmitting surface.

(Appended Mode 2)

The wide angle optical system according to appended mode 1, wherein the direction of the chromatic aberration of magnification which occurs is same for all light beams passing along the first optical path and all light beams passing along the second optical path.

(Appended Mode 3)

A wide angle optical system having a first optical path along which light from an object in front passes, a second optical path along which light from an object on a side passes, and a common optical path along which the light from the object in front and the light from the object on a side pass, comprising in order from a side of the object in front:

a first lens group having a negative refractive power;
a second lens group having a catadioptric optical element;
an aperture stop; and
a third lens group having a positive refractive power, wherein
the first lens group includes a positive lens and a negative lens, and
the catadioptric optical element has a first surface, a second surface, and a third surface that is formed between the first surface and the second surface, and
the first surface has a first transmitting surface and a first reflecting surface, and
the first transmitting surface is formed to include an optical axis of the first optical path, and
the first reflecting surface is an annular reflecting surface, and is formed around the first transmitting surface, and
the second surface has a second transmitting surface and a second reflecting surface, and
the second transmitting surface is formed to include the optical axis of the first optical path, and
the second reflecting surface is an annular reflecting surface, and is formed around the second transmitting surface, and
the third surface has a third transmitting surface, and
the third transmitting surface is a side surface of a circular truncated cone, and
an apex of the circular truncated cone is positioned on the side of the object in front of the first lens group, and
in the first optical path, the first lens group, the first transmitting surface, and the second transmitting surface are positioned in order from the side of the object in front, and
in the second optical path, the third transmitting surface, the second reflecting surface, the first reflecting surface, and the second transmitting surface are positioned in order from the side of the object on a side, and
the aperture stop and the third lens group are positioned in the common optical path, and
a sign of an angle of incidence for all light beams incident on the third transmitting surface is same.

According to the present invention, it is possible to provide a wide angle optical system in which the chromatic aberration of magnification has been corrected favorably.

As described heretofore, the present invention is useful for a wide angle optical system in which the chromatic aberration of magnification has been corrected favorably.

What is claimed is:
1. A wide angle optical system, comprising:
a first optical path along which light from an object in front of the wide angle optical system passes;
a second optical path along which light from an object on a side of the wide angle optical system passes; and
a common optical path along which the light from the object in front and the light from the object on a side pass, wherein
the wide angle optical system includes in order from a side of the object in front, a first lens group having a negative refractive power, a second lens group having a catadioptric optical element, an aperture stop, and a third lens group having a positive refractive power, and
the first lens group includes a positive lens and a negative lens, and
the catadioptric optical element has a first surface, a second surface, and a third surface that is formed between the first surface and the second surface, and
the first surface has a first transmitting surface and a first reflecting surface, and
the first transmitting surface is formed to include an optical axis of the first optical path, and
the first reflecting surface is an annular reflecting surface, and is formed around the first transmitting surface, and
the second surface has a second transmitting surface and a second reflecting surface, and
the second transmitting surface is formed to include the optical axis of the first optical path, and
the second reflecting surface is an annular reflecting surface, and is formed around the second transmitting surface, and
the third surface has a third transmitting surface, and the third transmitting surface is a side surface of a circular truncated cone, and an apex of the circular truncated cone is positioned on the side of the object in front of the first lens group, and in the first optical path, the first lens group, the first transmitting surface, and the second transmitting surface are positioned in order from the side of the object in front, and in the second optical path, the third transmitting surface, the second reflecting surface, the first reflecting surface, and the second transmitting surface are positioned in order from the side of the object on a side, and the aperture stop and the third lens group are positioned in the common optical path, and the following conditional expressions (1), (2), and (3) are satisfied:

$$\upsilon p < \upsilon n \quad (1),$$

$$|\phi p| < |\phi n| \quad (2), \text{ and}$$

$$90° - \theta k < \alpha/2 \quad (3)$$

where, $\upsilon p$ denotes Abbe number for the positive lens, $\upsilon n$ denotes Abbe number for the negative lens, $\phi p$ denotes a refractive power of the positive lens, $\phi n$ denotes a refractive power of the negative lens, $\theta k$ denotes the minimum half angle of view for the second optical path, and $0° < \theta k < 90°$, and $\alpha$ denotes an apex angle of the circular truncated cone.

2. The wide angle optical system according to claim 1, wherein the following conditional expression (4) is satisfied:

$$0.7 < (|\phi n|/\upsilon n)/(\phi p/\upsilon p) < 1.5 \quad (4)$$

where, $\upsilon p$ denotes Abbe number for the positive lens $\upsilon n$ denotes Abbe number for the negative lens, $\phi p$ denotes the refractive power of the positive lens, and $\phi n$ denotes the refractive power of the negative lens.

3. The wide angle optical system according to claim 1, wherein the following conditional expressions (5) and (6) are satisfied:

$$35 < \upsilon n \quad (5)$$

$$\upsilon p < 35 \quad (6)$$

where, $\upsilon p$ denotes Abbe number for the positive lens, and $\upsilon n$ denotes Abbe number for the negative lens.

4. The wide angle optical system according to claim 1, wherein the third lens group includes a lens that moves in an optical axial direction.

5. The wide angle optical system according to claim 4, wherein a lens nearest to image in the third lens group is fixed.

6. The wide angle optical system according to claim 4, wherein the wide angle optical system is a zoom lens system having a wide angle end and a telephoto end, wherein the following conditional expression (7) is satisfied:

$$0.7 < |f3/fi| < 1.2 \quad (7)$$

where, f3 denotes a focal length of the third lens group at the wide angle end, and fi denotes a focal length of the lens that moves in the optical axial direction.

7. The wide angle optical system according to claim 4, wherein by the lens which moves in the optical axial direction, it is possible to switch to an observation of the object in front and the object on a side and to an observation of only the object in front.

* * * * *